(12) United States Patent
Atreya et al.

(10) Patent No.: US 11,951,217 B2
(45) Date of Patent: Apr. 9, 2024

(54) INACTIVATION OF PATHOGENS IN EX VIVO BLOOD PRODUCTS IN STORAGE BAGS USING VISIBLE LIGHT

(71) Applicants: The United States of America, as represented by the Secretary, Department of Health and Human Services, Bethesda, MD (US); The University of Strathclyde, Scotland (GB)

(72) Inventors: Chintamani Atreya, Bethesda, MD (US); Michelle Maclean, Scotland (GB); John G. Anderson, Scotland (GB); Scott J. MacGregor, Scotland (GB)

(73) Assignees: The United States of America, as represented by the Secretary, Department of Health and Human Services, Bethesda, MD (US); University of Strathelyde, Glasgow (GB)

( * ) Notice: Subject to any disclaimer, the term of this patent is extended or adjusted under 35 U.S.C. 154(b) by 188 days.

(21) Appl. No.: 17/750,108

(22) Filed: May 20, 2022

(65) Prior Publication Data
US 2022/0273834 A1 Sep. 1, 2022

Related U.S. Application Data

(63) Continuation of application No. 15/765,424, filed as application No. PCT/US2016/054508 on Sep. 29, 2016, now abandoned.
(Continued)

(51) Int. Cl.
*A61L 2/00* (2006.01)
*A61L 2/08* (2006.01)

(52) U.S. Cl.
CPC ............ *A61L 2/0052* (2013.01); *A61L 2/084* (2013.01); *A61L 2202/122* (2013.01); *A61L 2202/22* (2013.01)

(58) Field of Classification Search
CPC .. A61L 2/0052; A61L 2/084; A61L 2202/122; A61L 2202/22
See application file for complete search history.

(56) References Cited

U.S. PATENT DOCUMENTS

| 6,190,609 B1 | 2/2001 | Chapman et al. |
| 6,986,867 B2 | 1/2006 | Hanley et al. |
| (Continued) | | |

FOREIGN PATENT DOCUMENTS

| DE | 4209509 | 6/1993 |
| EP | 0457196 | 11/1991 |
| (Continued) | | |

OTHER PUBLICATIONS

Atreya et al., "Proceedings of the Food and Drug Administration public workshop on pathogen reduction technologies for blood safety 2019," *Proceedings of FDA Workshop*, 24 pages (Nov. 29, 2018).

(Continued)

*Primary Examiner* — Sean E Conley
*Assistant Examiner* — Brendan A Hensel
(74) *Attorney, Agent, or Firm* — Klarquist Sparkman, LLP

(57) ABSTRACT

Disclosed herein are methods and devices for the inactivation of pathogens (e.g., bacteria, viruses, etc.) in ex vivo stored blood products, such as plasma and/or platelets, by means of directing visible light radiation from an illuminating device into blood product storage containers in order to achieve effective pathogen inactivation without the presence of an added photosensitising agent in the blood product. An (Continued)

exemplary apparatus includes a control unit that operates a light source that emits light in the wavelength region of about 380-500 nm which is directed onto blood product storage bags at sufficient intensity to penetrate the bag material and the opaque blood product therein in order to inactivate pathogens in the blood product but at dose levels that cause no significant detrimental effects on the blood product.

19 Claims, 11 Drawing Sheets

Related U.S. Application Data

(60) Provisional application No. 62/236,706, filed on Oct. 2, 2015.

(56) References Cited

U.S. PATENT DOCUMENTS

| | | | |
|---|---|---|---|
| 8,778,263 B2 | 7/2014 | Walker et al. | |
| 2003/0085173 A1* | 5/2003 | deGheldere | A61L 2/0082 210/264 |
| 2004/0021089 A1 | 2/2004 | Cimino et al. | |
| 2007/0009377 A1 | 1/2007 | Goodrich et al. | |
| 2008/0305004 A1* | 12/2008 | Anderson | A61N 5/06 422/22 |
| 2010/0246169 A1 | 9/2010 | Anderson et al. | |
| 2011/0278467 A1 | 11/2011 | Tanaka | |
| 2015/0359921 A1 | 12/2015 | Palmer | |
| 2016/0324996 A1 | 11/2016 | Bilenko et al. | |
| 2019/0070323 A1 | 3/2019 | Atreya et al. | |

FOREIGN PATENT DOCUMENTS

| | | |
|---|---|---|
| EP | 1693072 | 8/2006 |
| WO | WO 99/59645 | 11/1999 |
| WO | WO 00/74731 | 12/2000 |
| WO | WO 2007012875 | 2/2007 |
| WO | WO 2009/056838 | 5/2009 |

OTHER PUBLICATIONS

International Search Report and Written Opinion for related International Application No. PCT/US2016/054508, dated Apr. 19, 2017, 16 pages.

"Laser Beam Products—Precision Optics," https://laserbeamproducts.wordpress.com/2014/06/19/reflectivity-of-aluminium-us-visible-and-infrared/, 2 pages (Jun. 19, 2014).

Maclean et al., "Inactivation of Bacterial Pathogens Following Exposure to Light from a 405-nm LED Array," *Applied and Environmental Microbiology*, 75(7): 1932-1937 (Apr. 2009).

McDonald, "405 nm light exposure of osteoblasts and inactivation of bacterial isolates from arthroplasty patients: potential for ne disinfection applications?" *eCM Journal*, 25:204-214 (Mar. 7, 2013).

Schubert et al., "Ultraviolet-Based Pathogen Inactivation Systems: Untangling the Molecular Targets Activated in Platelets," *frontiers in Medicine*, 10 pages (May 7, 2018).

* cited by examiner

INACTIVATION OF PATHOGENS IN EX VIVO BLOOD PRODUCTS IN STORAGE BAGS USING VISIBLE LIGHT

CROSS-REFERENCE TO RELATED APPLICATIONS

This application is a continuation of U.S. patent application Ser. No. 15/765,424 filed Apr. 2, 2018, which is the U.S. National Stage of International Application No. PCT/US2016/054508 filed Sep. 29, 2016, which claims the benefit of U.S. provisional patent application No. 62/236,706 filed Oct. 2, 2015, all of which are incorporated by reference herein in their entirety.

FIELD

This application is related to methods and devices for inactivating pathogens in ex-vivo stored blood and blood products.

BACKGROUND

Bacterial and viral contamination of ex vivo stored human blood and blood components is a major complication for transfusion medicine, resulting in discarding of the products, and health risks for recipients of contaminated donor blood. Current pathogen reduction technologies (PRT) rely on the use of chemicals and/or ultraviolet light; however reported adverse events, and concerns about the PRT-treated blood components quality and toxicity, have limited the routine use of PRT worldwide.

For plasma treatment, a number of PRTs have been developed and pathogen-reduced plasma is routinely used, with several of these methods now licensed for use in North America and Europe. The original PRTs developed for plasma treatment included the use of solvent/detergent, and methylene blue in combination with visible light. More recently developed methods have employed ultraviolet (UV) light. Exposure to amotosalen (S-59) plus long-wave ultraviolet (UVA) light, and treatment with riboflavin and UV light, have been developed to treat both plasma and platelets. Many current PRTs have limitations and affect plasma coagulation factors and inhibitors of homeostasis to varying degrees, and concerns about reduced component quality and toxicity have limited or prevented the routine use of PRTs in many countries.

For platelet components, bacterial contamination still poses the highest risk of transfusion-transmitted disease despite the availability of bacterial detection methods. Although platelets usually have very low levels of bacterial contamination at the time of donation, platelets are stored at room temperature and this allows bacterial proliferation to occur throughout the storage period. Over a 5 day storage period even extremely small numbers of contaminating bacteria can multiply to very high and clinically dangerous levels.

A challenge for PRTs with platelet products is to maintain biological function of the treated cells, while achieving adequate pathogen reduction levels. For platelets this means sufficient retention of adhesive, aggregating and procoagulant properties to restore hemostasis in the recipient. Platelet treatment methods that have been developed include amotosalen/UVA treatment and riboflavin/UV-light treatment. While data of clinical and hemovigilance studies indicate that the overall safety profile of pathogen-reduced platelets is comparable to that of conventional platelets, there have been concerns over acute respiratory distress associated with UV light and photosensitizer-treated platelets.

Because of these uncertainties regarding currently available PRTs for plasma and platelet treatments, and because the full extent of future microbiological challenges cannot be predicted, methods to improve existing pathogen reduction technologies and the introduction of novel technologies remains an active area of investigation in transfusion medicine.

SUMMARY

The technology disclosed herein provides a new solution for the decontamination of blood products that overcomes limitations associated with currently available PRTs. This disclosure describes, for example, the application of violet-blue light centered around 405 nm wavelengths for pathogen reduction in blood products such as plasma and platelets. Unlike previous methods that require the decontamination treatment of the blood product prior to deposition in the storage container, methods described herein permit decontamination to take place after the blood products enter the final storage receptacle, thereby minimizing any unnecessary further contamination from environmental sources during subsequent transfer operations.

Another aspect of the technology is that, unlike previous PRTs which utilize light radiation from the ultra-violet (UV) region of the spectrum, disclosed technologies utilize radiation from the visible light spectrum, such as with wavelengths particularly within the range of 380-420 nm and especially at or around 405 nm. This is beneficial as it permits inactivation of pathogens to occur without the photochemical damage to sensitive blood product components caused by high energy UV-light photons associated with UV light. In addition, visible light has longer wavelengths that can more efficiently penetrate through blood storage bags and through the opaque blood products at lower intensities and without damaging the storage bag material. Moreover it does not require the addition of chemical photosensitising agents which can also have a deleterious impact on the quality of blood products.

The disclosed technology makes use of properties of visible light, which have somewhat greater penetrability powers than UV light, thereby permitting the concept of in situ treatment of bagged products by enabling penetration of light through the transparent bag material and into the stored product. The low transmissibility property of blood plasma and platelets is shown in FIG. 2.

One aspect of the disclosed technology is to combine the use of a sufficient level of irradiation of visible light into the product which is mixed by agitation to a sufficient extent that the blood product circulates within the container and effective decontamination of most of or substantially the entire product volume is achieved. Agitation also prevents aggregation of platelets and other blood components.

Another aspect is the specification of the levels of irradiation needed to achieve the desired decontamination effect. For an LED light source emitting light at 405 nm with bandwidth of ~10 nm, for example, the irradiance level at the blood product surface is desirably within a certain range that inactivates pathogens but does not harm the blood products (such as at least 3 $mWcm^{-2}$ and less than 80 $mWcm^{-2}$), with exposures ranging from minutes to hours, depending on the level of irradiance used. Use of higher irradiance levels enables faster treatment times, e.g. for rapid treatment (of the order of minutes), and use of lower irradiance levels facilitates longer treatment, e.g. for background decontamination during standard storage conditions (of the order of hours). These values can permit effective microbial decontamination of the blood product without causing any significant deleterious effects on blood product components. Hence in some embodiments, the blood products do not contain chemical photosensitization agent additives.

Also disclosed herein is an exemplary apparatus for inactivating pathogens in ex vivo stored blood products. The apparatus includes a treatment chamber configured to receive at least one sealed container storing a blood product, and at least one light source operable to emit light that is directed to a blood product storage container in the treatment chamber. The emitted light has a wavelength or wavelength spectrum and an intensity sufficient to penetrate through a wall of the container and into the blood product, such that the irradiance of the light reaching the blood product inside the wall of the container is sufficient to inactivate pathogens in the blood product without the presence of an added photosensitizing agent in the blood product and without a detrimental effect on the blood product, such that the blood product is suitable for future medical use. The treatment chamber can include a viewing window that filters out the treatment light wavelengths and allows other visible light wavelengths to pass through so that an operator can see inside the chamber. The chamber can include reflective walls, lenses, diffusers, and/or other optical features for directing light at the blood storage containers. The containers can rest on a tray in the chamber that vibrates or otherwise agitates the blood product in the container to prevent aggregation and/or to circulate the blood product inside the container for increased radiation exposure. The blood product containers can also be suspended in the chamber or positioned in other orientations. Light sources can be positioned on different sides of the container to expose more than one surface of the container at the same time. The apparatus can include any of various other features, such as a fan, air circulation system, temperature monitoring system, sensors, and a control system that controls the light sources and other active features of the apparatus.

The foregoing and other objects, features, and advantages of the disclosed technology will become more apparent from the following detailed description, which proceeds with reference to the accompanying figures.

DETAILED DESCRIPTION

Explanation of Terms

Figure 1A:
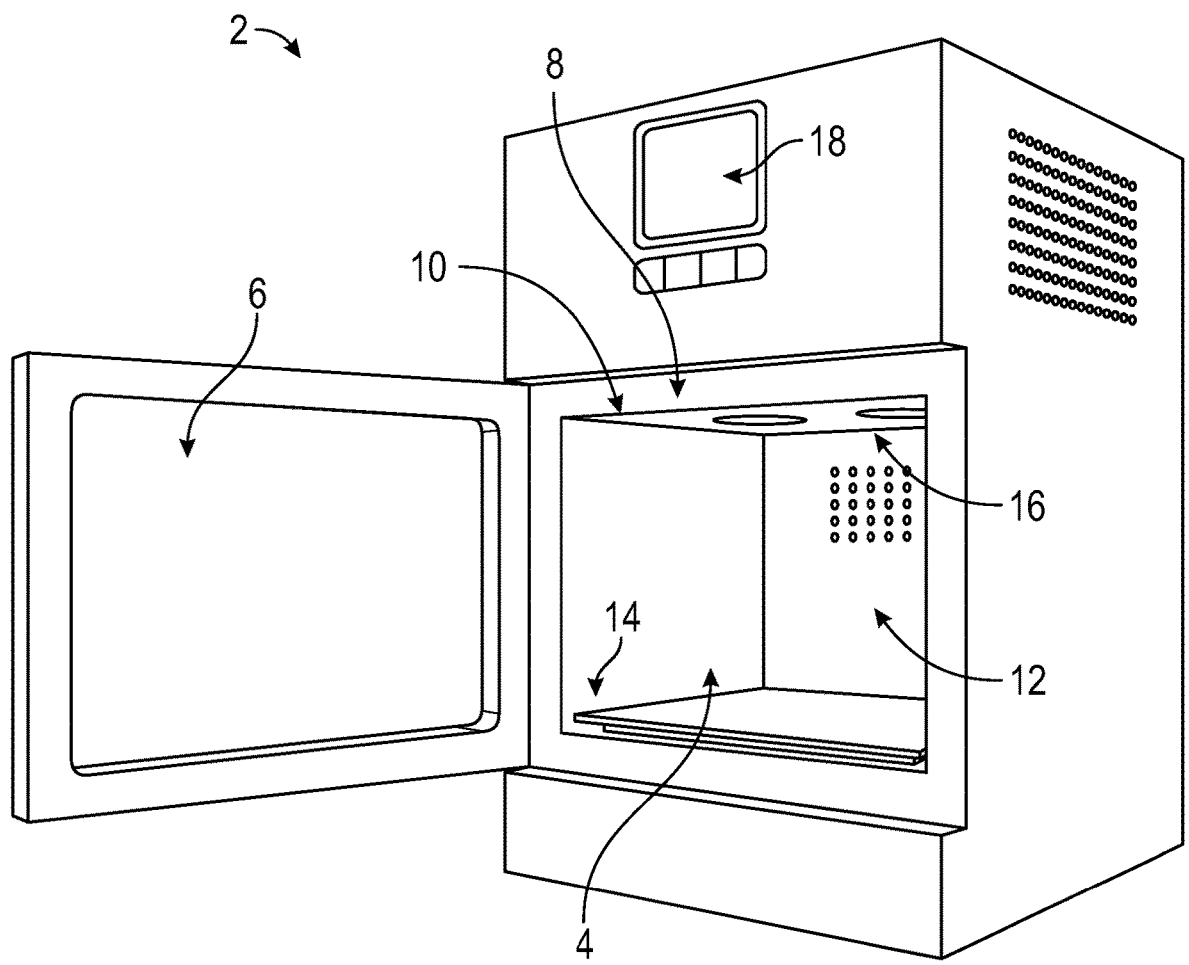
FIG. 1A is a perspective view of an exemplary treatment chamber for inactivating pathogens in stored blood products.

The disclosed technology can be used to treat any of various stored blood products. As used herein, the term "blood products" includes whole blood, plasma, platelets, red blood cells, fluids comprising any of these substances, and/or fluids derived from any of these substances. The terms "blood" and "blood products" includes human, animal, and/or synthetic blood and blood products.

As used herein, the terms "pathogen" and "contaminant" and "contaminant microorganism" are used interchangeably and include any undesired bacteria, viruses, fungi, viroids, parasites, and/or other contaminant microorganisms present in a blood product. The term "bacteria" includes Gram positive types of bacteria, such as *Staphylococcus*, *Streptococcus*, *Bacillus*, *Clostridium*, *Enterococcus*, etc., species and also includes Gram negative types such as *Escherichia*,

*Pseudomonas, Klebsiella, Acinetobacter*, etc., species. The term "fungi" includes single celled fungi such as yeasts and filamentous or spore forms such as mold fungi. The term "virus" includes any of the various types of viruses that can be present as contaminants in blood products.

As used herein, the term "inactivation" means that the subject microorganisms/pathogens are killed, damaged, and/or otherwise affected so as to inhibit or prevent their ability to replicate, infect a subject, and/or cause disease. For example, inactivation of a pathogen including viruses and other microorganisms stated in the above paragraph can include damaging the pathogen's genetic material that includes for example DNA, RNA, non-coding small RNAs (ncRNAs including microRNAs), and long non-coding RNAs (lnRNAs), thereby inhibiting its ability to reproduce, replicate and/or multiply. Methods disclosed herein can therefore be considered, in some cases, as bactericidal/fungicidal/viricidal or bacteriostatic/fungistatic/virustatic and this may depend on the species/strain of bacteria or virus, wavelength of light, dose, and/or other factors.

Pathogen levels in blood products can be measured in terms of colony forming units, or "CFU", which is an estimate of the number of pathogens (e.g., cells, viruses, etc.) in a given volume of blood product that are viable and can multiply, reproduce, or replicate.

As used herein, the term "light" means electromagnetic radiation having specified wavelength properties. If not specifically limited to particular wavelength properties, "light" includes electromagnetic radiation having wavelengths from about 1 nm to about 1 mm, including ultraviolet (UV) light, visible light, and infrared (IR) light. The term "visible light" includes electromagnetic radiation having wavelengths from about 380 nm to about 800 nm. The term "violet-blue light" means electromagnetic radiation having wavelengths from about 380 nm to about 500 nm. The term "wavelength" means the length of one full wave or spatial period of the electromagnetic radiation, and can be defined as the inverse of the radiation's frequency.

As used herein, the terms "irradiance" and "intensity" are used interchangeably to mean the radiant flux received by a given surface per unit area, measured in watts per square meter ($W/m^2$). Radiant flux is the radiant energy emitted/transmitted/received per unit time, and is measured in watts or joules per second. The term "radiation dose" or "light dose" means the product of the irradiance and the duration of exposure, and can be measured in joules per square meter ($J/m^2$).

Light emitted or received can include a range of different wavelengths, and the light at each wavelength can have a different spectral irradiance. "Spectral irradiance" is the irradiance of a surface per unit wavelength. Often, light has a greatest spectral irradiance at a certain wavelength, and reduces in spectral irradiance at longer or shorter wavelengths, such as in a "bell curve" shaped pattern. The wavelength or wavelength range having the greatest spectral irradiance is referred to herein as the center wavelength or center wavelength range of the light, such that the light is referred to herein as being "centered on or around" the center wavelength or center wavelength range.

As used herein, the term "photosensitizing agent" means any chemical additive, not naturally present in blood, that is added to a blood product and that produces a chemical change in another molecule in a photochemical process. Exemplary photosensitizing agents include riboflavin, benzoporphyrin derivative-monoacid ring A (BPD-MA), phenothiazine derivative methylene blue and other dyes with photochemical properties including psoralens, such as S-59 (amotosalen-HCl) and S-303 or the ethylene imine PEN-110.

As used herein, the term "detrimental effect" means a substantial change in the normal physiological condition of a stored blood product (e.g., a substantial reduction in the ability of platelets to rapidly aggregate in response to TRAP introduction). Further, the phrase "without detrimental effect on the blood product" means without causing a substantial change in the normal physiological condition of the blood product.

Exemplary Methods, Systems, and Devices

According to one aspect of the disclosed technology, there is provided methods and devices that utilize visible light at a wavelength and irradiation sufficient to inactivate pathogens (e.g., bacteria, viruses, fungi, viroids, prions, parasites) that are present in stored human and animal blood products, such as whole blood, plasma and platelets.

According to another particularly beneficial aspect, the disclosed technology utilizes visible light wavelengths (e.g., violet-blue light) without the use of an added photosensitising agent. Hence, in some embodiments a photosensitizing agent is not added to the blood products. Also since disclosed methods utilize visible light, this avoids the chemical and physical damage caused by the conventional methods of exposure to the higher energy photons of UV light.

According to another aspect of the disclosed technology, there is provided a method for inactivating bacteria, fungi, viruses, and/or other pathogens that can be present as contaminants in blood products, comprising exposure of the blood products to visible light having wavelengths in the range 380-500 nm. The light may have wavelengths in the range 400-450 nm. The light may have wavelengths in the range 380-420 nm. The light may have a wavelength spectrum centered on or around 405 nm. In some embodiments, at least 50% or at least 90% of the light has a wavelength within any of the disclosed ranges. In some embodiments, at least 50% or at least 90% of the light has a wavelength within 10 nm of 405 nm.

According to another aspect of the disclosed technology there is provided a method and apparatus for the inactivation of pathogens in blood products while these are contained within sealed blood storage containers, such as blood transfusion bags. Microbicidal wavelengths of light are used that penetrate through the storage bag material and to sufficient depth within the blood product as to achieve effective pathogen inactivation over an exposure period.

An exemplary treatment device 2 is illustrated in FIG. 1A. The device 2 comprises an exposure chamber 4 wherein sealed blood product storage bags, or similar storage containers, are placed for treatment. The device 2 includes a door 6 that closes the treatment chamber and is configured to prevent some or all of the light of the selected emission wavelengths (e.g., 380-500 nm) from escaping from the treatment chamber. The door 6 can include a viewing window to observe the treatment process. The window can comprise a light filter (e.g., amber tinted) that allows certain visible wavelengths to pass through (e.g., 500-800 nm) and blocks shorter wavelengths. The door 6 can also include an automatic light turn-off system that turns off the lights when the door is opened.

The device 2 can utilize a lighting system 8 which can comprise one or more LED sources 10 and/or other types of light sources that emits light in a selected wavelength range and intensity sufficient to inactivate pathogens in stored blood products. The lighting system 8 can be configured to deliver light in any direction above, below and/or to the sides of the stored blood products in order to achieve focused or uniform illumination of the blood products as required. For example, light sources can be mounted on any surface of the chamber and/or on shelves, racks, trays, and/or other structures within the chamber. Blood storage bags can thereby be irradiated from two or more different directions, such as from the top and bottom, or two other opposing sides, at the same time.

Figure 1B:
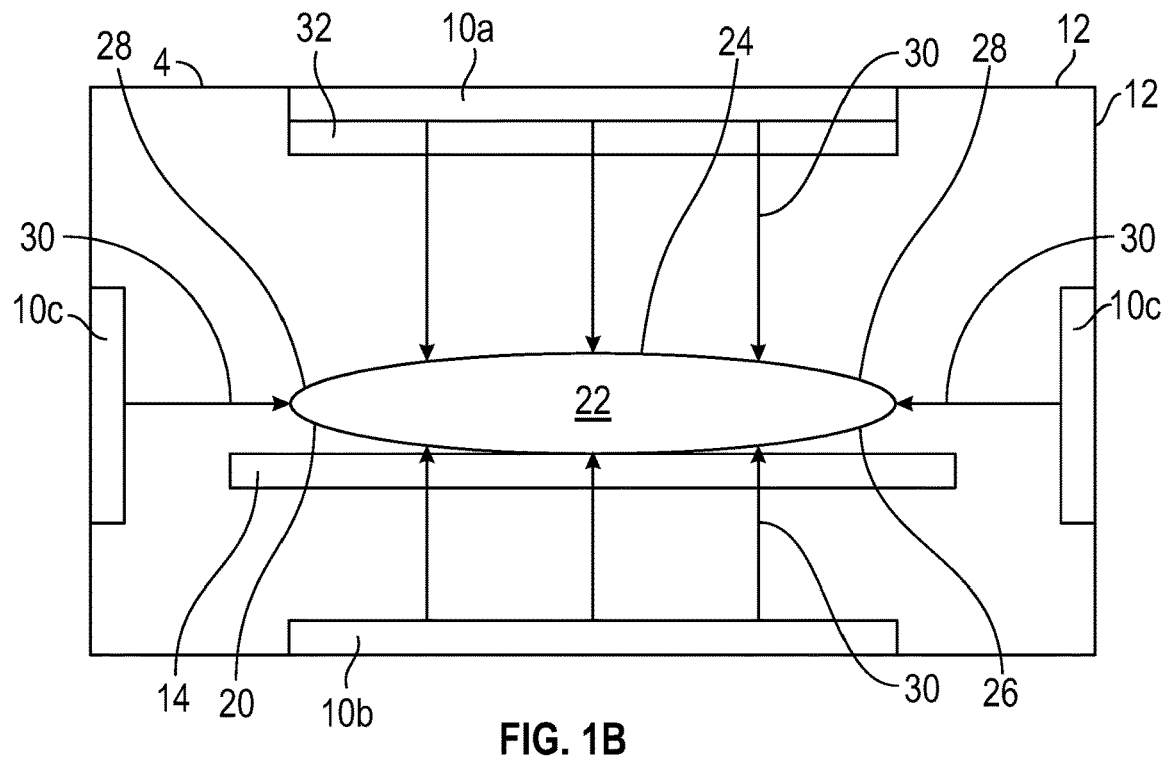
FIG. 1B is a schematic view of an exemplary treatment chamber having various light sources, a tray, and a blood product storage container on the tray being irradiated with light from the light sources.
Figure 1C:
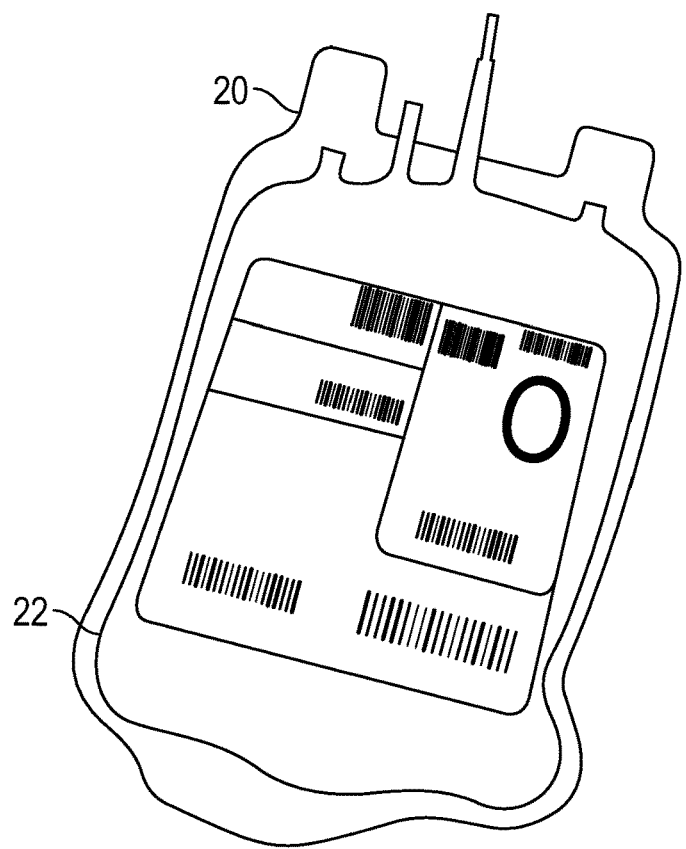
FIG. 1C shows an exemplary blood product storage container.

FIG. 1B is a schematic view of an exemplary treatment 4 chamber of the device 2 with a storage container 20 containing a blood product 22 resting on a tray 14. FIG. 1C shows an exemplary blood product storage container filled with a blood product. As shown in FIG. 1B, the chamber 4 includes plural light sources, including an upper light source 10A, a lower light source 10B, and side light sources 10C. In a cuboid chamber, all four vertical walls can include light sources. Each light source emits light 30 that is directed to the storage container 20. The light 30 can reach and pass through some or all of the walls of the container 20, including the upper wall 24, lower wall 26, and side walls 28. In some embodiments, some of the light 30 can pass through the tray 14, such as to reach the lower wall 26. In some embodiment, the chamber 4 can also include reflective inner surfaces 12 to enhance irradiation of the container 20. The arrangement in FIG. 1B is only one non-limiting example, and various other arrangements can be utilized in other embodiments.

The treatment chamber 4 can have various dimensions, even up to the size of an entire room, in which the lighting system 8 is installed at one or more locations around the treatment chamber, and the internal surfaces 12 of which can be lined with or made from highly reflective material. Exemplary reflective materials include various mirrored surfaces, polished stainless steel, polished aluminum, silver coated surfaces, various retroreflective material surfaces and surfaces that are optimal for reflecting light of wavelengths between 380-500 nm and/or 400-420 nm and/or 405 nm.

According to another aspect of the disclosed technology, the treatment device can include a mechanically operated reciprocating tray or platform 14 on which stored blood products may be continuously agitated during exposure to the inactivating light. Agitation can help circulate the blood product inside the container for a more even irradiation and/or to reduce aggregation of platelets or other blood components. The reciprocating tray or platform 14 can be operated at different reciprocation rates (e.g., 10-100 rpm or 30-100 rpm) and for differing periods of time throughout the duration of the light treatment in order to provide sufficient mixing so that the opaque blood product receives sufficient light treatment within the illuminated zone under the semi-transparent bag material. As shown, the device 2 includes one tray 14, though in other embodiments the device can include two or more independent trays, such as trays that are stacked on top of each other and/or side-by-side. In some embodiments, the tray 14 or trays can be at least partially transparent or transmissive of the treatment light wavelengths such that blood product bags can be irradiated from below while resting on a tray. In embodiments with multiple trays, the light sources can be arranged and positioned around the chamber roof, walls, floor, and/or on the tray bottoms to provide the desired light exposure to the blood products on each tray. In various embodiments, the treatment chamber 4 can simultaneously contain two or more blood product containers in any relative orientation, such as lying side-by-side flat on one or more trays, one above the other on different trays, suspended from above or hanging, etc.

According to another aspect, the device 2 can comprise a temperature control system, ventilation system, and/or air circulation system 16 in order to accurately control the environment inside the chamber 4 throughout the treatment process.

According to another aspect of the disclosed technology, the lighting system 8 can include lenses or diffusers positioned adjacent to the light sources 10 in order to achieve directed or diffuse light outputs depending on the process requirements. For example, FIG. 1B illustrates an exemplary lens and/or diffuser 32 coupled to the upper light source 10A. This can provide a more even light distribution and/or a more focused light exposure to a particular area.

According to yet another aspect of the disclosed technology, the lighting system 8 can deliver light at different intensities during the treatment period so that, for example, a high radiation dose may be delivered at the beginning of the process to achieve effective initial inactivation followed by a lower dose regime to maintain the decontamination effect. Predetermined intensity patterns and cycles can be used during a treatment. Other variations in dose delivery may also be used, such as depending upon the blood product type and nature of the pathogens present. For example, the intensity of the light emitted from the light sources can be sufficient such that irradiance levels at the surface of the blood product within the storage container can be from about 3 $mWcm^{-2}$ to about 80 $mWcm^{-2}$ in some embodiments. In some embodiments, the light reaching the surface of the blood product has an irradiance of 3 $mWcm^{-2}$ or less. In some embodiments the light reaching the surface of the blood product has an irradiance of 80 $mWcm^{-2}$ or greater. In some embodiments, the light emitted from the light sources can have any of the irradiance or intensity values provided herein, or greater values due to the reduced area of the light sources relative to the blood product. In some embodiments, the light reaching the external surface of the blood product storage container can have any of the irradiance or intensity values provided herein. In various embodiments, the light reaching at least some portion of the blood product within the storage container can have any of the irradiance or intensity values provided herein. The irradiance of the light can decrease as it passes through the storage container material, and thus the irradiance at the surface of the blood product can depend on the material and thickness of the storage container walls, as well as various other factors.

According to yet another aspect of the disclosed technology, the device 2 can have a lighting control system 18 that allows for the setting or programming of different irradiation intensities and durations throughout the blood product treatment period. The control system 18 can control the chamber air temperature and/or humidity, air circulation, tray agitation/vibration, light source selection, light source intensity, treatment duration, cycles, patterns, and/or automatic light source turn-off (e.g., when door is open or temperature is too high). The control system 18 can also include or be coupled to one or more sensors that measure desired properties and provide feedback to the control system 18. Exemplary sensors or sensor systems can include temperature sensors, light intensity or irradiance sensors, light wavelength or frequency sensors, tray weight sensors, and/or other sensors.

Exemplary Investigations, Results, and Analysis

Figure 2:
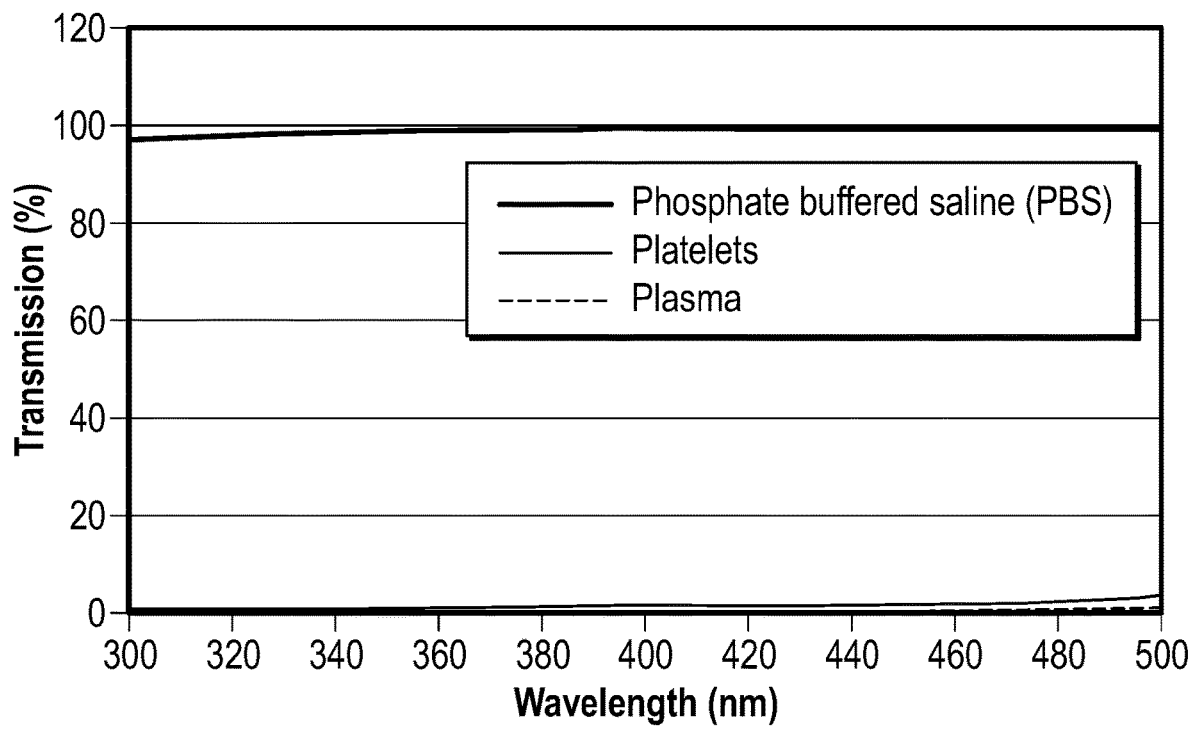
FIG. 2 shows the percent transmission of 300-500 nm light through phosphate buffered saline (PBS), plasma and platelets. Transmittance is almost 100% through PBS at this wavelength but very low for platelets and plasma.

To investigate the effects of visible light, and particularly 405 nm light, on pathogens in stored blood products, the optical properties of blood, blood plasma, platelets, and other blood products were initially determined. To do this, spectrophotometric analysis was carried out over the wavelength range 220-700 nm using a Biomate 5 UV-Visible Spectrophotometer. The results shown in FIG. 2 demonstrate that light transmission through plasma and platelets is below 5% over the 300-500 nm wavelength range, compared to >95% for a clear liquid such as phosphate buffered saline (PBS). Nevertheless, use of sufficiently high dose levels, multi-direction irradiation, agitation, and/or other techniques can be used to at least partly overcome transmissibility limitations of blood products.

The effectiveness of the visible light for inactivating pathogens in blood products was investigated by seeding bacteria into test liquids and then exposing them to visible light irradiation. Bacteria used in these tests were *Staphylococcus aureus, Staphylococcus epidermidis* and *Escherichia coli* and these were selected to represent significant contaminants associated with blood components.

The use of the bacteria described above was for illustrative purposes only. In addition, a wide range of other pathogens are susceptible to visible light, including 405 nm light. For example, Gram-positive and Gram-negative bacteria, yeasts, fungi, bacterial endospores and viruses can be inactivated by 405 nm light and/or other visible light, with up to 9-log reduction in populations demonstrated. Such pathogens can be successfully inactivated when suspended in blood products such as plasma and platelets when exposed to inactivating doses of 405 nm light and/or other visible light having bandwidths near 405 nm.

Disclosed devices and methods can be used for decontamination (e.g., inactivation of pathogens) of blood products, either within test containers or within blood transfusion storage bags. To test the effect of visible light on the inactivation of bacteria in selected blood products, defrosted fresh frozen human plasma and human platelets were seeded with known concentrations of bacterial contaminants. The light source used for exposure was an array of 405 nm LEDs powered by a direct current supply. For thermal management, the LED arrays were bonded to a heat sink and fan, thus ensuring that heating had no effect on the test samples exposed to the 405 nm light.

To demonstrate the principle, three different sample volumes (3 ml, 30 ml and approximately 300 ml (whole transfusion bags)) were used for exposure. For exposure of 3 ml samples, samples were held in 12-well microplates (without the lid), with the LED array positioned 3 cm above, providing an irradiance at the sample surfaces of ~100 mWcm$^{-2}$. 30 ml samples were exposed in 90 mm dishes (lid on), with the LED array positioned above to provide an irradiance of ~8 mWcm$^{-2}$. For exposure of platelet and plasma bags, LED arrays were held above the horizontally-positioned bags to give an irradiance of 3-5 mWcm$^{-2}$ at the center position of the bag. Experimental systems were held in a shaking incubator (72 rpm; 25° C.) for continuous sample agitation to maintain exposure conditions. After light exposure, samples were plated onto growth medium, incubated, and enumerated to determine the number of surviving colony-forming units (CFU)/ml. The light dose (J cm$^{-2}$) used to expose the blood samples was calculated as the product of the irradiance (W cm$^{-2}$) multiplied by the exposure time (sec).

Figure 3:
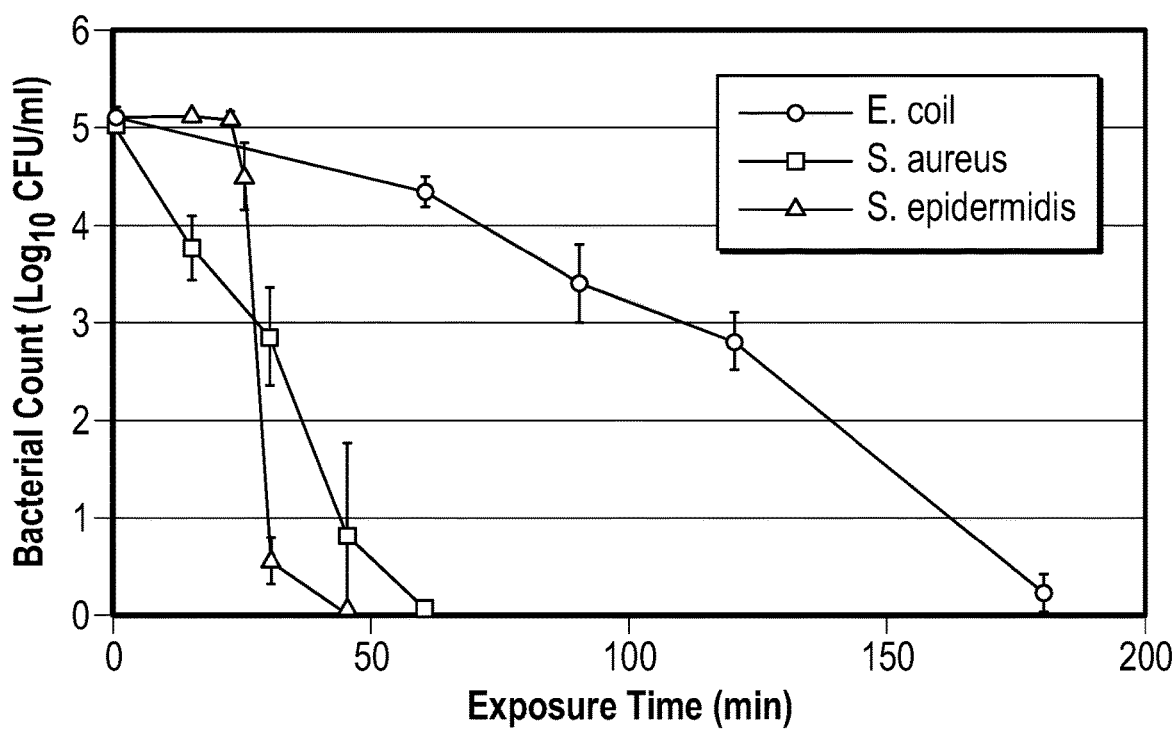
FIG. 3 shows an example of the effect of 100 mWcm$^{-2}$ 405 nm light on the CFU count of *Staphylococcus epidermidis*, *Staphylococcus aureus* and *Escherichia coli* suspended in human plasma at a population density of $10^5$ CFUml$^{-1}$.
Figure 4:
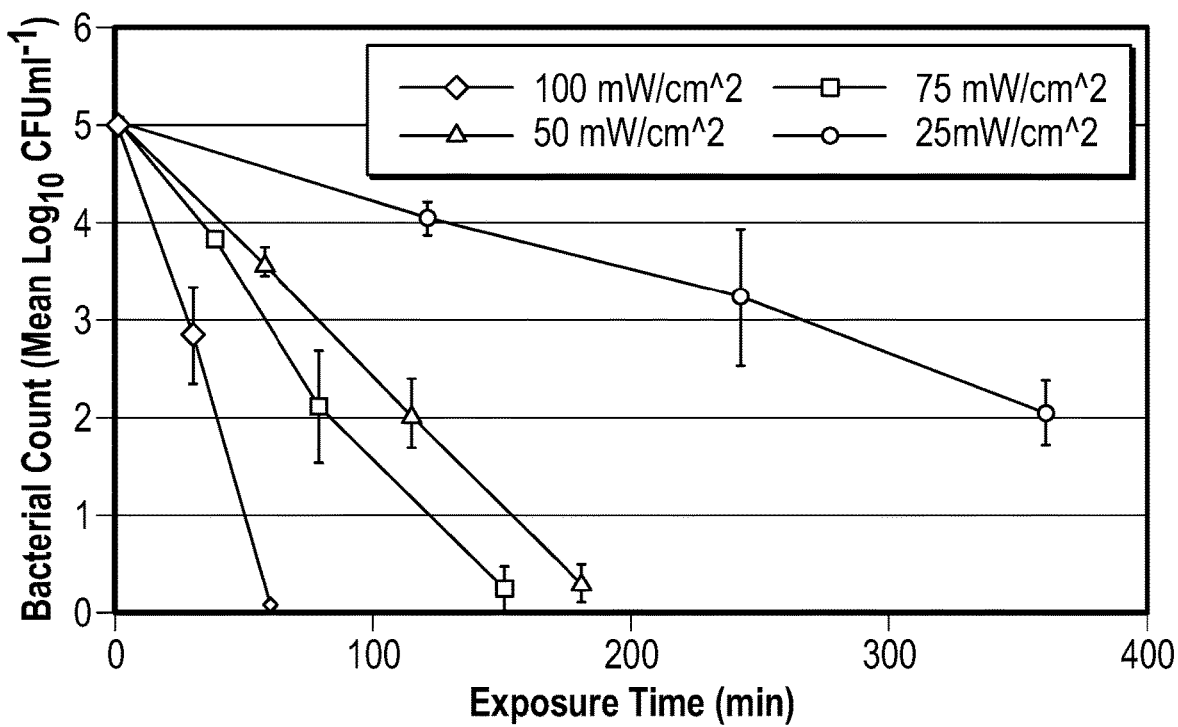
FIG. 4 is a plot of the effect of 405 nm light of differing irradiances on $10^5$ CFUml$^{-1}$ populations of *Staphylococcus aureus* suspended in human plasma.

FIG. 3 shows the effects of 100 mWcm$^{-2}$ 405 nm light for inactivation of *S. aureus, S. epidermidis* and *E. coli* in human plasma. Near complete inactivation of *S. aureus* was achieved after 45 min (270 Jcm$^{-2}$). Exposure experiments repeated using lower irradiances of light (75, 50, 25 mWcm$^-$2) also demonstrated significant population reductions, with use of higher irradiance resulting in increased inactivation rates (FIG. 4). Similar inactivation kinetics were observed for *S. epidermidis*. Test data on *E. coli* also demonstrated that reduction of *E. coli* contamination can be achieved.

Figure 5:
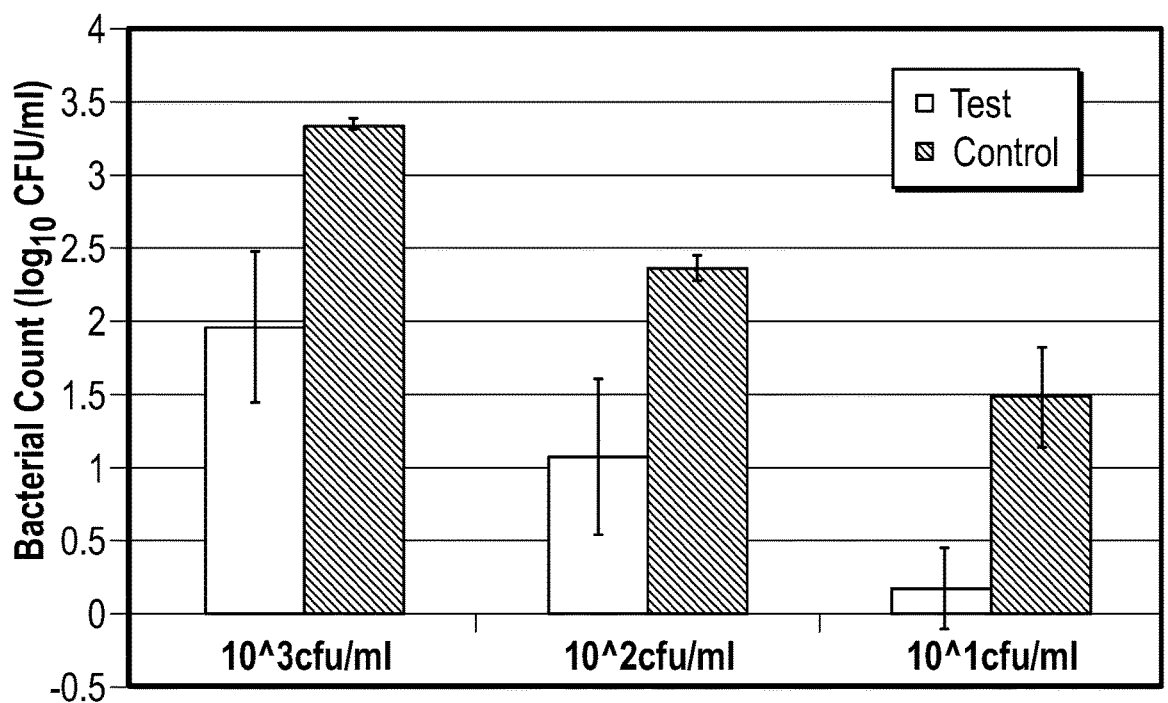
FIG. 5 is a plot of inactivation of $10^1$, $10^2$ and $10^3$ CFU/ml *S. aureus* in 3 ml platelet suspensions by exposure to 100 mW/cm$^2$ 405 nm light for 2-hr.

Tests carried out using 3 ml volumes of platelets seeded with different levels of bacterial contamination also demonstrate the ability of light of this wavelength to inactivate microbial contamination in platelets. FIG. 5 shows the results from exposing 3 ml platelets seeded with *S. aureus* to 2-hr 100 mW/cm$^2$ 405 nm light. Successful inactivation was achieved in all cases, with approximately 1.5 log$_{10}$ reductions being achieved after a 2-hr exposure to 100 mW/cm$^2$ light. Near-complete inactivation of 10$^1$ CFU/ml contamination was observed. Use of a longer exposure period results in complete inactivation of the 10$^2$ and 10$^3$ CFU/ml contamination levels as was shown by use of a 4-hr exposure period, where near complete inactivation (<5 CFU remaining) of a 10$^3$ CFU/ml population was achieved (data not shown).

Pathogens suspended in clear media, such as phosphate buffered saline (PBS), can be inactivated using lower doses of visible light. The need for higher doses in the case of inactivation in blood plasma and platelets can be accredited to the differing optical properties of these suspending media. The opacity, and consequent relatively low transmissibility of plasma and platelets (FIG. 2), reduces photon penetration through the suspension, resulting in the need for greater doses, compared with suspension in clear, transparent liquids such as PBS. Despite this, these results demonstrate that significant inactivation of bacterial contaminants in human plasma can be achieved using visible light, such as light centered on or around 405 nm, with the higher the irradiance of light applied, the shorter the exposure time needed for successful inactivation. Ultraviolet light and other shorter-wavelength light, on the other hand, does not penetrate as well through opaque blood products, and consequently may not provide adequate inactivation of pathogens throughout a container under similar conditions.

Figure 6:
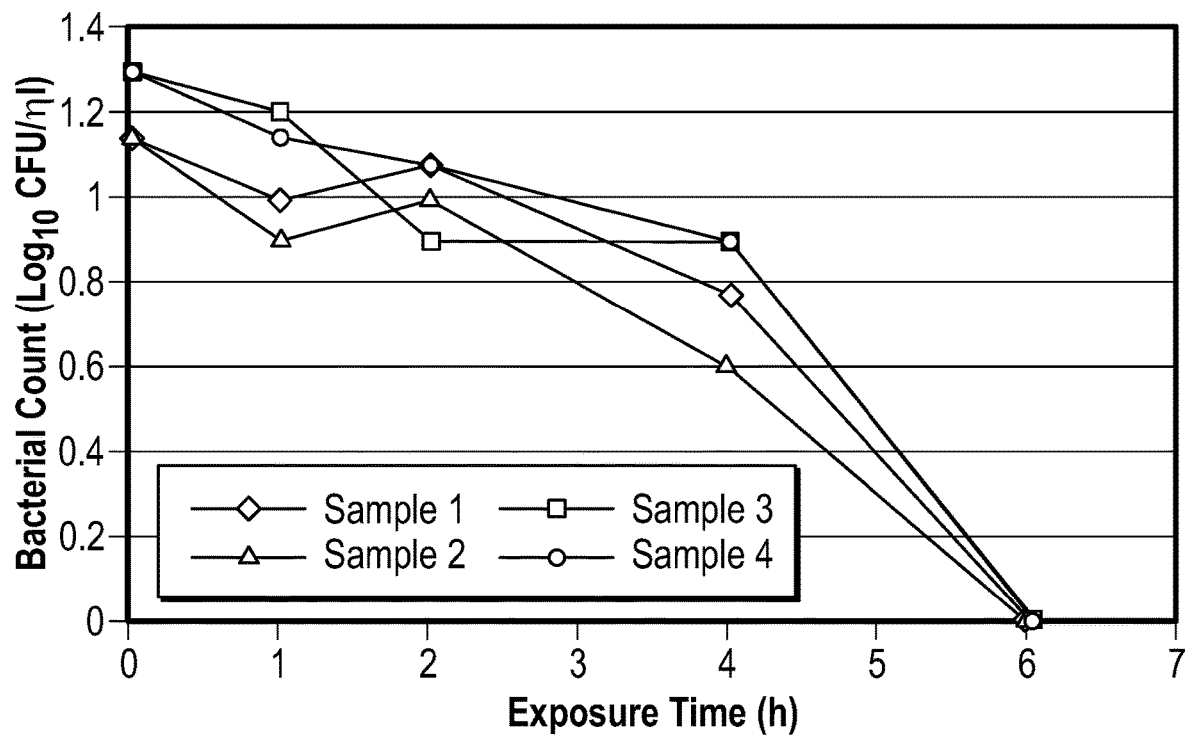
FIG. 6 is a plot of inactivation of $10^1$ CFU/ml *S. aureus* in 3 ml plasma using 14 mW/cm$^2$ 405 nm light.

In addition to using high (e.g., 100 mWcm$^{-2}$) irradiance levels at the blood product surface, experiments were carried out to establish that low density pathogen contamination (10$^1$ CFU/ml) can be inactivated when using a lower irradiance level, such as 14 mW/cm$^2$. Results, shown in FIG. 6, demonstrate that complete inactivation of the bacterial contamination within plasma samples was achieved after a 6-hr exposure period. Control contamination levels remained unchanged.

Figure 7:
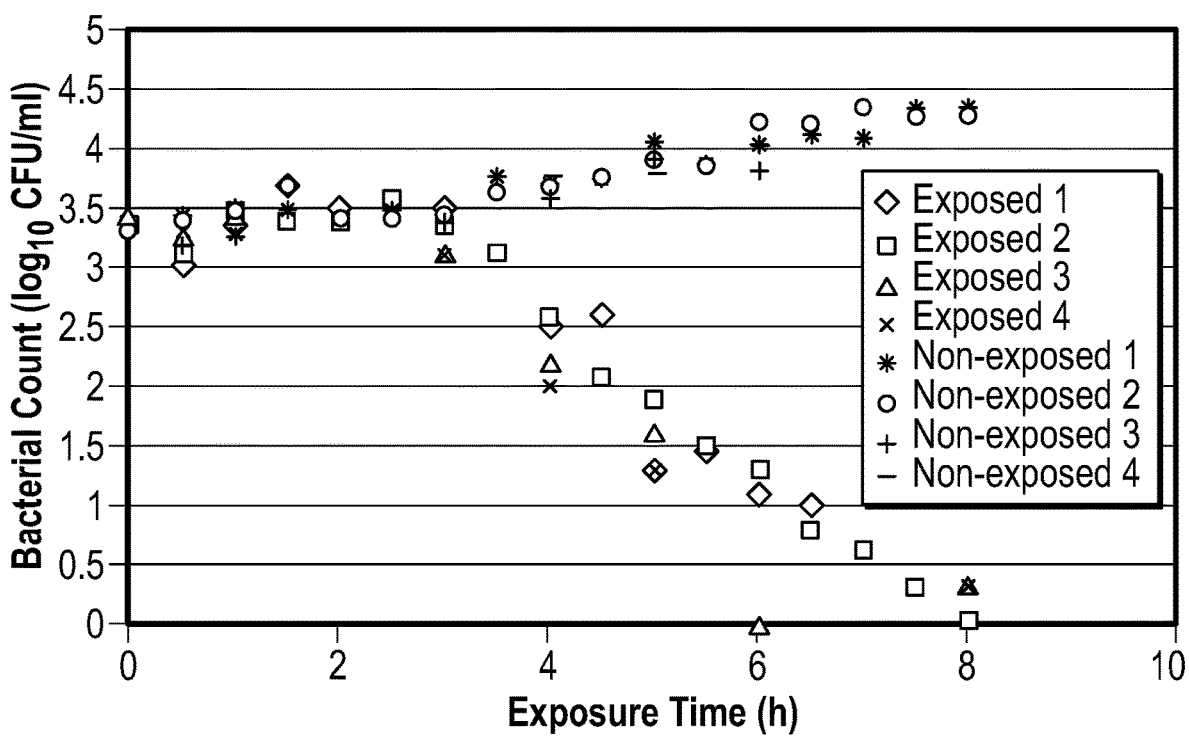
FIG. 7 is a plot of inactivation of *S. aureus* at a contamination level of $10^3$ CFUml$^{-1}$ in a 30 ml volume of human plasma held in a closed sample dish by exposure to ~8 mWcm$^{-2}$ 405 nm light.

To demonstrate that decontamination of larger volumes of plasma and platelets can be achieved (i) using lower irradiance visible light, and (ii) in sealed containers without the presence of an added photosensitizing agent, tests were conducted wherein 30 ml volumes of human plasma and platelets seeded with different levels of *S. aureus* were exposed, in a closed Petri dish, to an irradiance of ~8 mWcm$^{-2}$. An example of the results for plasma with a seeding density of 10$^3$ CFUml$^{-1}$ is shown in FIG. 7, and these results demonstrate that exposure of 8 hours at 8 mWcm$^{-2}$ (230 Jcm$^{-2}$ dose) induced near-complete inactivation. Similar results (not shown) were observed for inactivation of the 10$^2$ and 10$^1$ CFUml$^{-1}$ contamination levels, with near complete inactivation achieved with 187-230 Jcm$^{-2}$, and 201.6-230.4 Jcm$^{-2}$, respectively.

Figure 8:
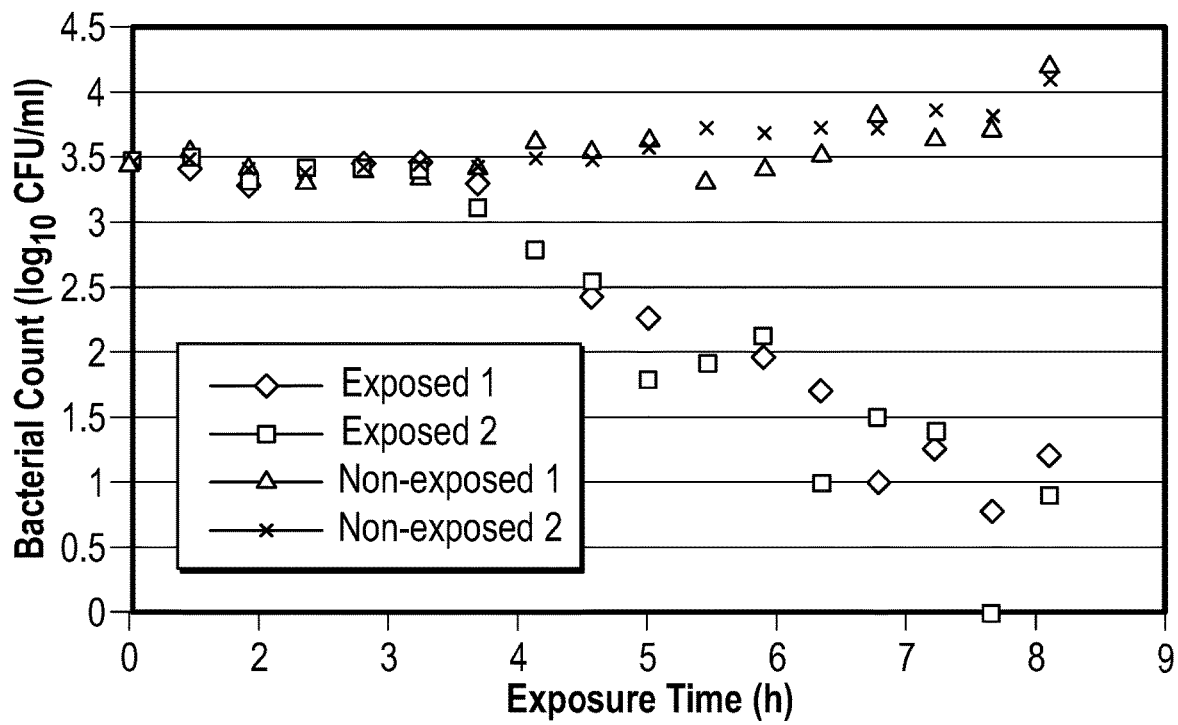
FIG. 8 is a plot of inactivation of *S. aureus* at a contamination level of $10^3$ CFUml$^{-1}$ in a 30 ml volume of human platelets held in a closed sample dish by exposure to ~8 mWcm$^{-2}$ 405 nm light.

FIG. 8 shows an example of the results demonstrating the inactivation of 10$^3$ CFU/ml *S. aureus* in 30 ml platelet suspension in a closed dish using an irradiance of ~8 mW/cm$^2$. Inactivation became evident after 115 Jcm$^{-2}$ (4-hr), with near-complete inactivation achieved over the 8-hr exposure period (230 Jcm$^2$). Tests were also carried out (results not shown) demonstrating faster inactivation with a 10$^2$ CFU/ml contamination level with near complete inactivation achieved by 201 Jcm$^{-2}$. Successful inactivation of 10$^1$ CFU/ml contamination levels was achieved with the fastest rate, with complete/near complete inactivation achieved by 4-hr exposure (115 Jcm$^2$). Overall, these experiments successfully demonstrated that low irradiance light can be used over prolonged time periods to inactivate low-level contamination in 30 ml volumes of plasma and platelet suspensions, in sealed containers.

Figure 9:
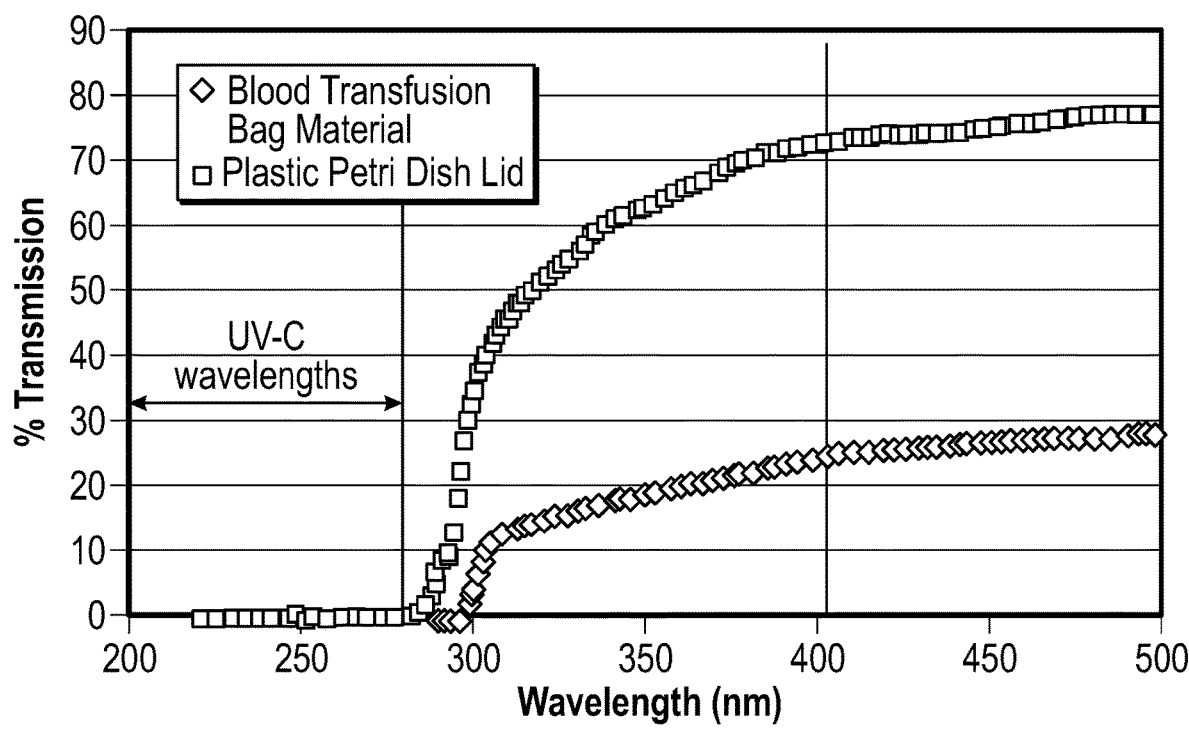
FIG. 9 is an optical analysis of transmission properties of the blood bag material and petri dish, highlighting 405 nm and UV-C light wavelengths for reference.

In order for the applied light to sufficiently affect the blood product, a sufficient amount of the applied light has to first pass through the storage container wall. For this reason, the transmissibility of blood product bag materials was measured and tested. FIG. 9 shows the transmissability of a typical PVC blood product storage bag wall, as well as comparable transmissibility of clear plastic Petri dish wall, over different wavelengths. The measurements demonstrate that transmission of 405 nm light though the blood product bag material resulted in an approximate 20-30% loss in irradiance. However, light irradiance can be increased through the use of higher power light sources in order to compensate for this loss if needed. Alternatively or additionally, a storage container can be irradiated from opposite surfaces of the container. Overall, these results show that 405 nm light, and visible light in general, can transmit through typical blood product bag materials, thus permitting decontamination of at least the adjacent portions of the blood product contained in the storage bag. The transmissibility of visible light through storage container walls is also a significant advantage over UVC-light and other shorter-wavelength light, which is blocked nearly completely by the PVC bag material as shown in FIG. 9.

Figure 10:
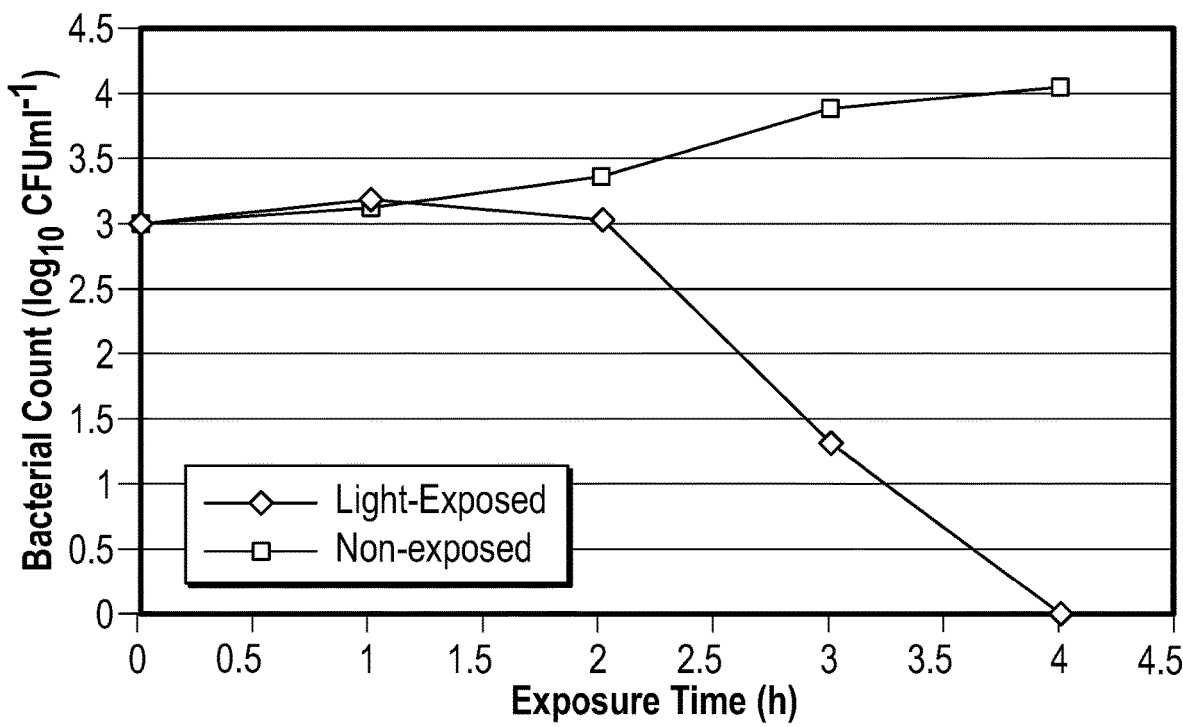
FIG. 10 is a plot of 405 nm light inactivation of *S. aureus* suspended in human plasma covered by a layer of blood bag material.

To further demonstrate the application of the disclosed technology, tests were carried out to establish that bacteria can be inactivated in human blood plasma when the applied light was transmitted through a layer of blood bag material. Tests were carried out by placing samples of the contaminated plasma into the wells of a 12-well microplate (without the lid), but with the wells covered with a layer of PVC blood-bag material, and the sample was exposed to 14 mWcm$^{-2}$ 405 nm light at the sample surface. Samples were treated in the rotary incubator (37° C.; 72 rpm). Exposure of *S. aureus* suspended in human plasma to 405 nm light transmitted through the blood-bag material resulted in successful inactivation with complete inactivation achieved after a 4-hour exposure period as shown in FIG. 10. The comparatively long exposure period in such cases can be attributed to the use of a low irradiance level of 14 mWcm$^{-2}$. Inactivation can be achieved more rapidly if a higher irradiance level is used for sample exposure.

Figure 11:
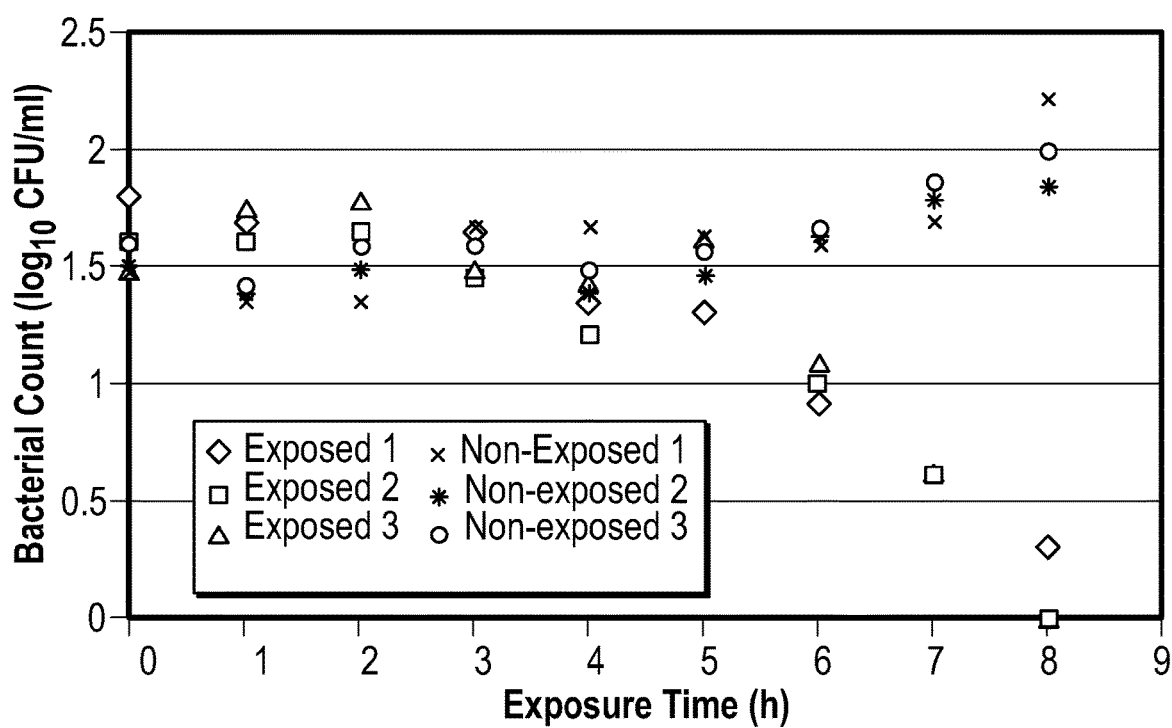
FIG. 11 is a plot of inactivation of *S. aureus* contamination in 300 ml transfusion bags of human plasma by exposure to 405 nm light using an irradiance of ~5 mWcm$^{-2}$.

To demonstrate the effectiveness of the disclosed technology for decontamination of plasma and platelets when these are contained within sealed blood bags, experiments were conducted to expose whole PVC transfusion bags, seeded with contamination, to 405 nm light. Inactivation of low density (10$^1$-10$^2$ CFU ml$^{-1}$) bacterial contaminants within PVC plasma transfusion bags was achieved using irradiances as low as 3 mWcm$^{-2}$ at the plasma surface. An example of inactivation using 5 mWcm$^{-2}$ at the plasma surface is shown in FIG. 11. A downward trend in contamination was observed after exposure for 6 h (108 Jcm$^{-2}$). Complete/near complete inactivation was achieved after exposure for 8 hr (144 Jcm$^{-2}$). This slightly reduced inactivation rate, compared to that found within the sample dishes, is due to the lower irradiance light being used for exposure: faster inactivation can be achieved using higher irradiance light, as shown in the 100 mWcm$^{-2}$ experiments.

Figure 12:
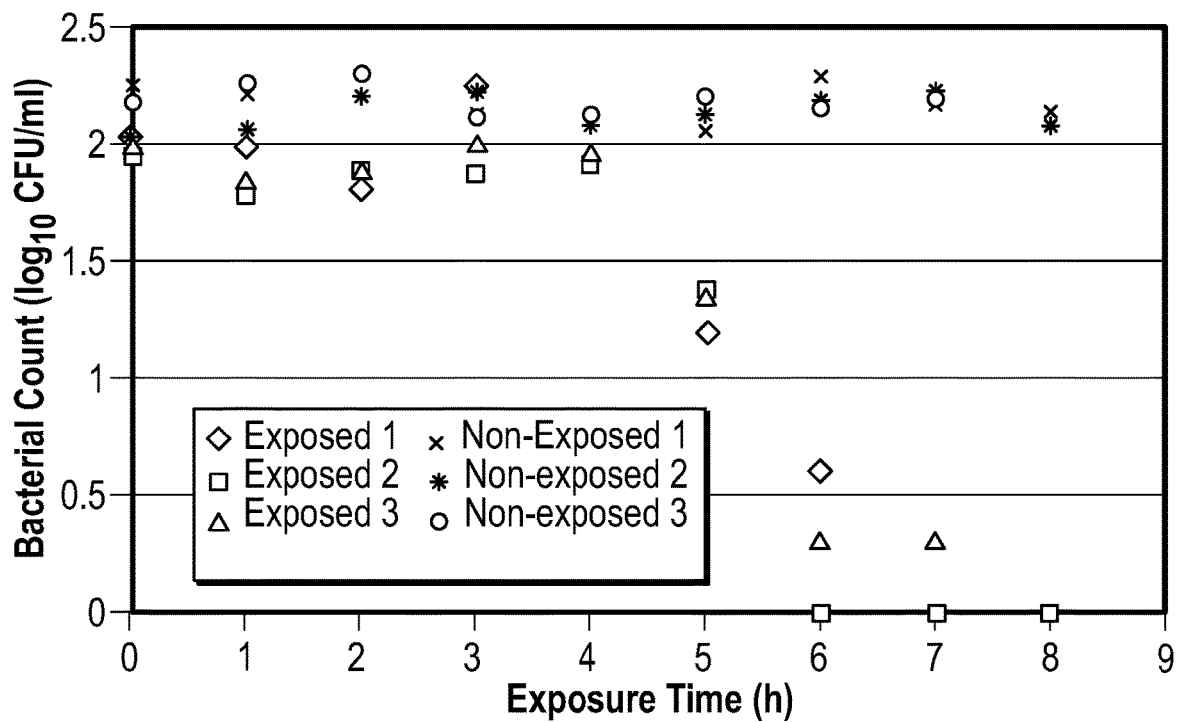
FIG. 12 is a plot of inactivation of ~$10^2$ CFU/ml *S. aureus* seeded into platelet bags (approx. 200 ml volume) using 3 mW/cm$^2$ 405 nm light.
Figure 13:
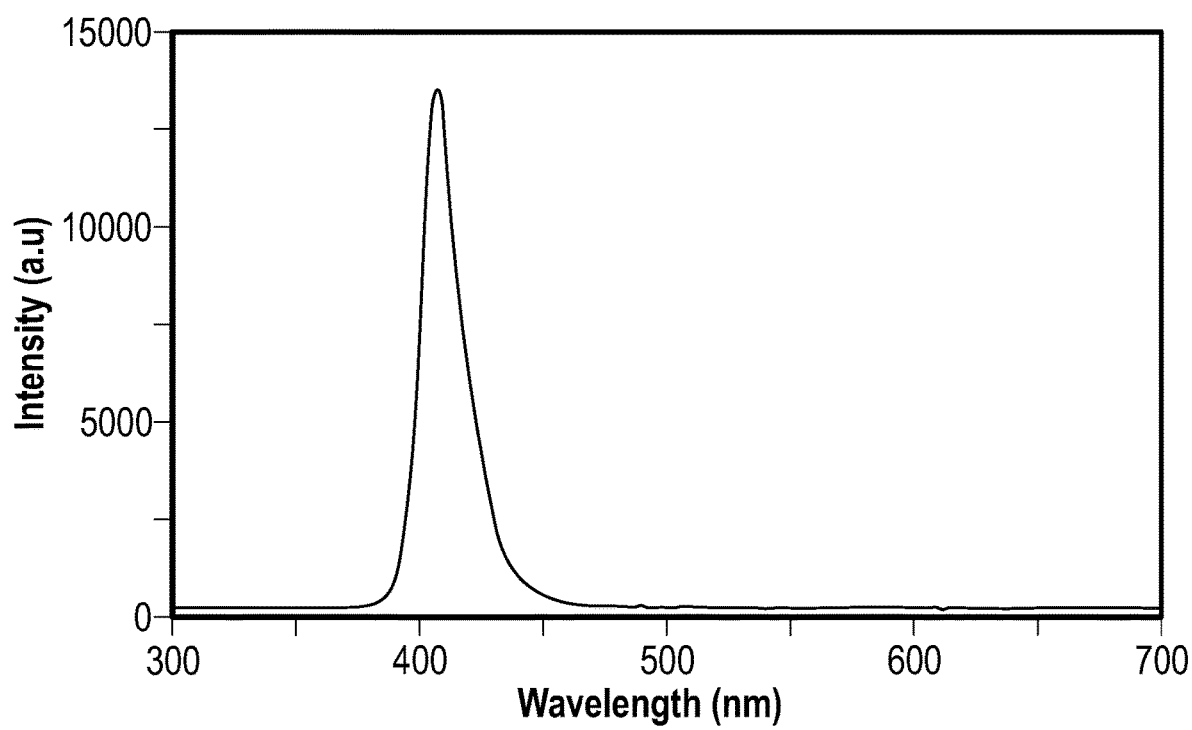
FIG. 13 shows the wavelength intensity spectrum for an exemplary light source centered around 405 nm discussed herein.

FIG. 12 shows the successful results of the use of 5 mWcm$^{-2}$ 405 nm light for inactivation of contamination within platelet bags. Results demonstrate that bacterial inactivation becomes evident after 5 h exposure (90 Jcm$^{-2}$), with complete/near complete inactivation being typically achieved by 6 hours (108 Jcm$^{-2}$). Control bacterial populations in the non-exposed samples demonstrated that the bacterial contamination either remains unchanged or increases slightly over the course of the 8-hour period, confirming that the inactivation effect was the result of the light exposure. The inactivation kinetics achieved when the bags were exposed to four different irradiance levels (3, 5, 7, 10 mWcm$^{-2}$—data not shown) appeared to follow similar trends, indicating that differences in irradiances in the region of 3-10 mW/cm$^2$ are not likely to have a major effect on the inactivation rates. This may be aided by the agitation of the bags during exposure, which facilitates circulation of the blood product and thus good illumination of the whole volume of blood product.

The preceding investigations and results demonstrate that the disclosed technology effectively inactivates pathogens contained within blood products, such as blood plasma and platelets. Furthermore the disclosed technology establishes that visible light and particularly 405 nm light can be used for inactivation of pathogens in plasma and platelets while these blood products are contained within transfusion bags. The fact that light of 405 nm wavelength can penetrate the transfusion bag material enables the blood products to be decontaminated (i.e., inactivation of pathogens) while sealed in the bags, thereby significantly reducing the risk of any post treatment contamination that can occur with other procedures.

When the disclosed technology is used as a platelet decontamination technology, it can be important that the visible light treatment has no adverse effects on the platelet cells, and that they are suitable for transfusion post treatment. Testing and establishing such features of the disclosed technology included the establishment of information about the physiological effects of visible light on platelet cells. To this end, the standard tests that are performed on platelets in blood bank storage conditions, such as platelet count, pH of the platelet solution, and platelet aggregation in response to platelet agonists [e.g. Thrombin Receptor Agonist Peptide (TRAP)], were evaluated following a selected time (in hours) of 405 nm light exposure of platelets in the bags (see Tables 1a, 1b and 1c below). Rapid aggregation associated with TRAP induction is a positive indicator that platelets are in normal physiological conditions during storage. Thus, the test to control ratio of 1 (i.e., 100%) or close to 1 (i.e., close to 100%) is a good indicator of the quality of platelets in any given context.

Analysis was performed using platelets processed from a donor split into two equal halves and each half was stored in a storage bag. At least two donor samples were used for each experiment (n=2), where feasible. For each 405 nm light exposure treatment, one platelet bag was used as control and the other as test sample. Platelet bags were exposed to three different treatment conditions: [1] At 10 mW/cm$^2$ 405 nm light for up to 6 hrs; [2] At 40 mW/cm$^2$ 405 nm light for up to 6 hrs; and [3] At 80 mW/cm$^2$ 405 nm light for up to 6 hrs. The non-exposed control samples (in a light-safe box) and the test samples were held under rotary conditions during exposure (~25° C. and 72 rpm) in the same incubation chamber. Samples were collected and analyzed at 2 h intervals from both light-exposed and control samples.

Tables 1a, 1b, and 1c below show platelet counts, pH measurements and TRAP-induced platelet aggregation of non-exposed platelets and platelet samples exposed to 405 nm light at 10 mW/cm$^2$ (Table 1a) 40 mW/cm$^2$ (Table 1b) and 80 mW/cm$^2$ (Table 1c) for up to 6 hrs while in transfusion bags. Note that "Control" and "Test" are two individual bags originated from the same donor and the same donation (split sample).

TABLE 1a (405 nm light 10 mW/cm$^2$)

| Exposure (h) | Platelet count (K/μl) | | pH | | TRAP-induced aggregation shown as test to control ratio (%) |
|---|---|---|---|---|---|
| | Control | Test | Control | Test | |
| 0 | 1295 | 1301 | 7.2 | 7.1 | 100* |
| 2 | 1295 | 1309 | 7.2 | 7.1 | 100* |
| 4 | 1288 | 1304 | 7.1 | 7.1 | 100 |
| 6 | 1277 | 1279 | 7.2 | 7.1 | 100 |

TABLE 1b (405 nm light 40 mW/cm$^2$)

| Exposure (h) | Platelet count (K/μl) | | pH | | TRAP-induced aggregation shown as test to control ratio (%) |
|---|---|---|---|---|---|
| | Control | Test | Control | Test | |
| 0 | 1936 | 1930 | 7.1 | 7.1 | 100* |
| 2 | 1932 | 1920 | 7.0 | 6.9 | 106 |
| 4 | 1925 | 1900 | 7.1 | 6.9 | 118 |
| 6 | 1916 | 1924 | 7.1 | 6.9 | 45 |

TABLE 1c (405 nm light 80 mW/cm$^2$)

| Exposure (h) | Platelet count (K/μl) | | pH | | TRAP-induced aggregation shown as test to control ratio (%) |
|---|---|---|---|---|---|
| | Control | Test | Control | Test | |
| 0 | 1634 | 1596 | 7.0 | 7.0 | 100* |
| 2 | 1490 | 1520 | 7.1 | 7.0 | 96 |
| 4 | 1481 | 1492 | 7.1 | 6.7 | 46 |
| 6 | 1476 | 1474 | 7.2 | 6.5 | 0 |

Overall, the results of the analytical studies carried out (platelet count, pH and TRAP-induced aggregation) on platelets exposed to 405 nm light show that there are no major physiological changes in the platelet cells when exposed in containers or transfusion bags to 405 nm irradiances at 10 mW/cm$^2$ for up to 6 hours (Table 1a), or 40 mW/cm$^2$ for 4 hours (Table 1b), or 80 mW/cm$^2$ for up to 2 hours (Table 1c). However, change in pH and TRAP-induced aggregation was prominent when 405 nm irradiance at 80 mW/cm$^2$ was extended to 6 hours. These irradiance levels and treatment times have been shown to successfully inactivate the low levels of microbial contamination that can occur in whole blood platelet and plasma transfusion bags due to the light transmission through the sealed bag material and into the stored product. These exposure conditions can be compatible with the typical storage conditions of the platelets, so that one application for the technology is to utilize a combined storage and treatment regime involving exposing the platelets to light having wavelength spectrum centered on or around 405 nm while agitating the platelets during storage until they are used for transfusion.

Some embodiments of the disclosed technology utilize high irradiance treatment (e.g., up to 80 mW/cm$^2$) for exposure of whole platelet/plasma bags in order to achieve shorter exposure periods (e.g. minutes) for the effective inactivation of pathogens in the blood products without having detrimental effects on the blood products. Results from the analysis of high irradiance light-exposed platelets showed that there were no significant detrimental changes apparent in the platelet suspensions. Accordingly, some embodiments of the disclosed technology utilize high-irradiance exposure of whole bags to enable platelet/plasma bags to be treated quickly (e.g., 30-60 mins) immediately after collection from the donor before being stored awaiting transfusion.

The disclosed technology can be used to treat blood products stored in many different types of storage containers comprising various materials, so long as the container provides at least some transmissivity to the applied light. Exemplary container/bag materials suitable for use with the disclosed technology include PVC (polyvinyl chloride), EVA (ethylene-vinyl acetate), PE (polyethylene), PP (polypropylene), PS (polystyrene), combinations of such materials, variations of such materials, and/or other at least partially light-transmissive materials.

Viral Inactivation

FIGS. 13-18 illustrate the efficacy of the disclosed technology for viral inactivation in blood products and other media. The following describes testing that was performed to validate the efficacy of the disclosed technology involving 405 nm light (see spectrum in FIG. 13) in inactivating feline calicivirus (FCV), which serves as a model for Norovirus (NoV), which is one of the most common causes of epidemic acute gastroenteritis and can be transmitted via food and water, person-to-person contact or environmental surfaces contacts. Environmental stability and resistance to disinfection further aids transmission of NoV, with viral particles detected on surfaces up to 42 days after contamination. If environmental decontamination is deficient this can lead to ward closures which has substantial operational and financial implications for health boards. NoV outbreaks in the healthcare setting and other densely populated areas such as nursing homes and schools and restaurants have driven the need for new decontamination systems. However, the antiviral efficacy of 405 nm light on medically important human and animal viruses was lacking and required investigation.

The study described here was designed to illustrate the interaction of narrowband 405 nm light with FCV as a model to study the antiviral effects of this light on NoVs. FCV was selected as a NoV surrogate, as there is currently no standardized cell-culture system for NoV. Our data demonstrates the influence of the suspending media, including biologically-relevant fluids, on viral susceptibility. As such, this study provides evidence of the antiviral efficacy and discusses the potential mechanism of 405 nm light viral inactivation.

Feline embryonic cells, strain FEA (Jarrett, Laird & Hay 1973) were cultured in Dulbecco's Modified Eagle's Medium (DMEM) supplemented with 10% fetal bovine serum (FBS), 2 mM L-glutamine, 1 mM sodium pyruvate and 240 U mL$^{-1}$ penicillin streptomycin (Gibco, Life Technologies, UK), to form 10% FBS-DMEM. Cells were maintained at 37° C. in 5% $CO_2$.

To prepare a virus pool of the FCV vaccine strain F9, virus inoculum (School of Veterinary Medicine, University of Glasgow) was added to FEA monolayers in 850 cm² cell culture roller flasks (Corning, USA). After 90-min incubation of the inoculated cells on a rotating roller stand at 37° C. in 5% $CO_2$, fresh culture medium was added and flasks incubated for 24 hours. This resulted in virus-induced destruction of nearly 90% of the cell monolayer.

The tissue culture supernatant, and medium from a single wash step, was collected from each roller bottle and subjected to two freeze-thaw cycles before clarification by centrifugation at 3300×g for 10 minutes. The virus-containing supernatant was then stored at −80° C. until required. The infectious titre of FCV was approximately $2 \times 10^7$ plaque forming units per millilitre (PFU $mL^{-1}$), determined by standard plaque assay techniques (Ormerod & Jarret 1978).

The light source used was a 405 nm light emitting diode (LED) array (ENFIS PhotonStar Innovate UNO 24; PhotonStar Technologies, UK) powered by a 40 V Phillips Xitanium LED Driver (Phillips, Netherlands). The array had a peak wavelength around 405 nm and a bandwidth of approximately 19 nm (FIG. 13) but will, for convenience, be referred throughout the following text as 405 nm light. The array was attached to a heatsink and cooling fan, to minimize heat transfer to test samples, so that no significant heating of the sample occurred. The light source was held on a PVC stand at a distance of 4 cm from the microbial samples, giving an irradiance of 155.8 mW $cm^{-2}$ at the sample surface (measured using a radiant power meter and photodiode detector (LOT Oriel, USA)).

FCV stock virus was defrosted at room temperature and diluted to $2 \times 10^5$ PFU $mL^{-1}$ in Dulbecco's phosphate buffered saline, supplemented with calcium and magnesium (DPBS; Hyclone, Thermo Fischer Scientific, UK). This was used as a 'minimal medium' (MM). 1.5 mL volumes of viral suspension were transferred into the central 4 wells of a 24-well plate (Techno Plastic Products, Switzerland) and the plate positioned on a raised stand, with the sample wells 4 cm directly below the light source and the plate lid kept on to prevent evaporation. Test samples were exposed to increasing doses of 405 nm light at room temperature, with the dose calculated as the product of irradiance (mW $cm^{-2}$)× exposure time (s). Control samples were set up under identical environmental conditions but without 405 nm light illumination. Post-exposure, FCV samples were immediately removed from the well and serially diluted in MM for enumeration by plaque assay.

Exposures were repeated with FCV suspended in 'organically-rich media' (ORM): DMEM, 10% FBS-DMEM, artificial saliva, artificial faeces and blood plasma. The artificial saliva was a modified version of that used by Margomenou et al. (2000) [5.2 g $NaHCO_3$, 0.88 g NaCl, 1.36 g $K_2HPO_4$, 0.48 g KCl, 2000 units α-amylase and 2 g pig gastric mucin (Sigma Aldrich, UK) in 1 L sterile water], and was adjusted to pH 7-7.5 to emulate the variability of pH in human saliva, and also to ensure no FCV inactivation occurred (Duizer et al. 2004b; Edgar et al. 2004). The artificial faeces was a modified version of that by Colon et al. (2015) [30 g inactivated yeast (Marigold, UK), 7 g physillum (Buy Whole Foods Online, UK), 11 g miso paste (Yutaka, UK), 8 g cellulose, 1.6 g NaCl, 0.8 g CaCl, 1.6 g KCl (Sigma Aldrich, UK) in 920 mL sterile water], and was also adjusted to pH 7. The modifications to the artificial saliva and faeces formulations were to ensure compatibility with the FEA cells. Fresh frozen human blood plasma was obtained from the Scottish National Blood Transfusion Service (SNBTS, UK), and defrosted before use. FCV was also exposed whilst suspended in MM supplemented with riboflavin, with and without tyrosine, tryptophan, pyridoxine and folic acid (used at the same concentrations as found in DMEM: 0.4, 104, 16, 4 and 4 mg $L^{-1}$ respectively).

Prior to experiments, 6-well cell culture plates (Thermo Fischer Scientific) were seeded with $7.5 \times 10^5$ FEA cells per well. 3 mL of the cell suspension in growth medium was pipetted into each well, and incubated at 37° C. in 5% $CO_2$ for 20-h, resulting in confluent monolayers.

Post-exposure of FCV, the growth medium was aspirated from the FEA cells and replaced with 1 mL FCV sample. Plates were co-incubated at 37° C. in a humidified 5% $CO_2$ incubator for 90-min, with the plates gently rocked every 15-min to ensure even distribution of the inoculum over each monolayer.

After the viral incubation period, the inoculum was aspirated and the well washed with medium (10% FBS-DMEM or DPBS) before adding 4 mL overlay mixture consisting of 2× supplemented DMEM 1:1 with 2× agarose. 2× supplemented DMEM was prepared using 20 mL from a filter sterilized stock of 10×DMEM, adding the same supplements as detailed earlier, plus 9.86 mL sodium bicarbonate solution (Gibco), and was made up to 100 mL with sterile water. 2× agarose was prepared by dissolving 2 g agarose (Sigma Aldrich) in 100 mL deionized distilled water and sterilized by autoclaving. The overlay was left to set before the plates were incubated for 44-48 hours at 37° C. in 5% $CO_2$.

Post-incubation, the monolayers were fixed and stained overnight with 0.5% crystal violet in 10% buffered neutral formalin. The agarose plugs and stain were then removed, the plates left to dry, plaques counted, and the virus infectivity titre expressed as PFU $mL^{-1}$.

The presence of porphyrins, or other components with the ability to absorb 405 nm light and emit fluorescence, within the suspending media was determined by fluorescence spectrophotometry. Media were freshly prepared and fluorescence measurements were carried out using a RF-5301 PC spectrofluorophotometer (Shimadzu, USA). Excitation was carried out at 405 nm and emission spectra recorded between 425-700 nm.

Data points represent mean results±standard deviation (SD), taken from triplicate independent experiments (n=3). The antiviral activity of 405 nm light was determined by calculating the reduction in the level of infectivity from the difference between $Log_{10}$ values for exposed and control samples. Significant differences were calculated using one-way ANOVA (Minitab 16 Statistical Software) with results found to be significant when P<0.05.

FCV was suspended in MM and ORM and exposed to increasing doses of 405 nm light at an irradiance of 155.8 mW $cm^{-2}$. Results (FIG. 14) show that when suspended in MM, significant FCV inactivation was achieved after exposure to 561 J $cm^{-2}$ (P=0.043), and relatively linear inactivation kinetics were observed, with a dose of 2.8 kJ $cm^{-2}$ required for a 3.9 $Log_{10}$ inactivation. The non-exposed control samples showed no significant change over the course of the experiment (P>0.05).

Antiviral efficacy was found to differ significantly when suspended in ORM. When exposed in 10% FBS-DMEM, a significantly lower dose was required for viral inactivation (FIG. 15), with a 4.8 $Log_{10}$ reduction achieved after a dose of 421 J $cm^{-2}$. As the presence of FBS in DMEM is thought to reduce the level of oxidation upon exposure to normal laboratory lighting (Grzelak et al. 2001), the exposure was repeated with FCV suspended in DMEM without FBS to observe any differences in inactivation kinetics. Although slightly less inactivation was observed with each applied dose, results (FIG. 15) demonstrate no significant differences in the inactivation kinetics of FCV when the virus is exposed in DMEM in the presence or absence of 10% FBS (P>0.05). Control samples showed no significant decrease (P>0.05).

Furthermore, components of DMEM have been shown to be photosensitive to light (Grzelak et al. 2001), therefore exposures were repeated with riboflavin added to MM with and without tyrosine, tryptophan, pyridoxine and folic acid in the same concentrations found in DMEM (see Table 2 below). Results demonstrated that exposure of FCV suspended in MM with riboflavin only resulted a 1.3 $Log_{10}$ reduction after 421 J cm$^{-1}$, however when all components were present enhanced inactivation occurred and a 5.1 $Log_{10}$ inactivation was achieved.

Figure 16:
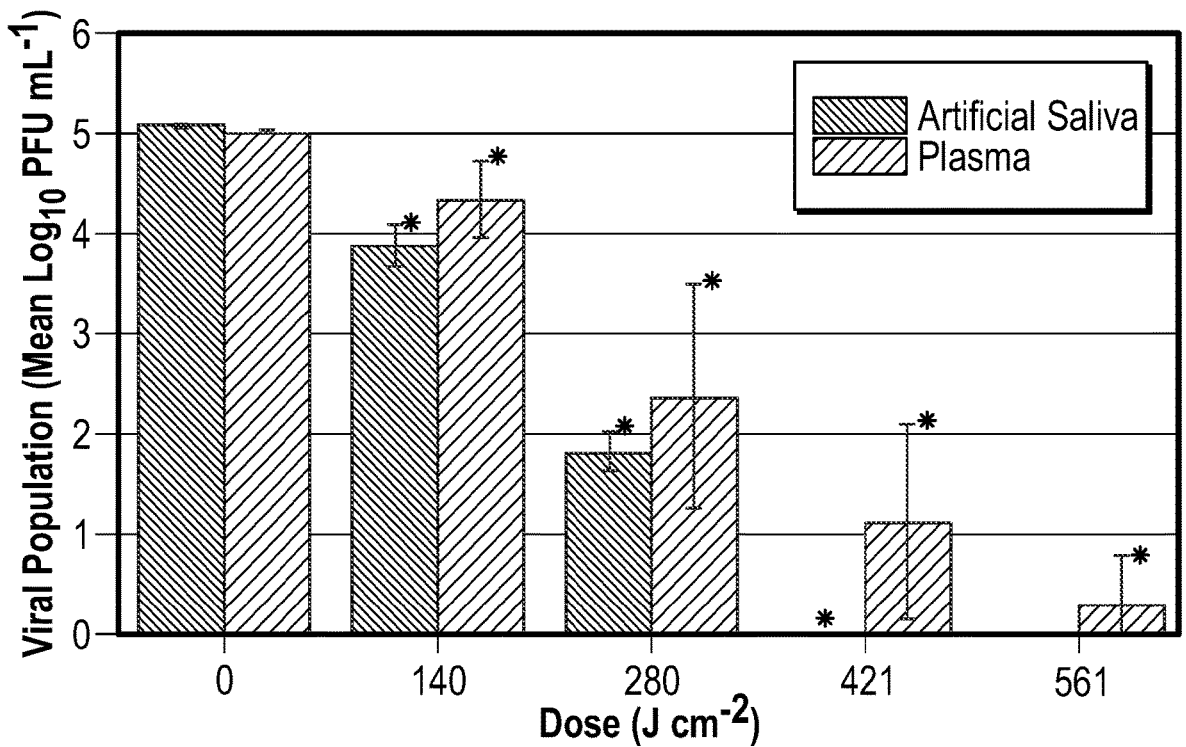
FIG. 16 shows decreasing FCV viral population in both artificial saliva and in blood plasma with increasing light doses.
Figure 17:
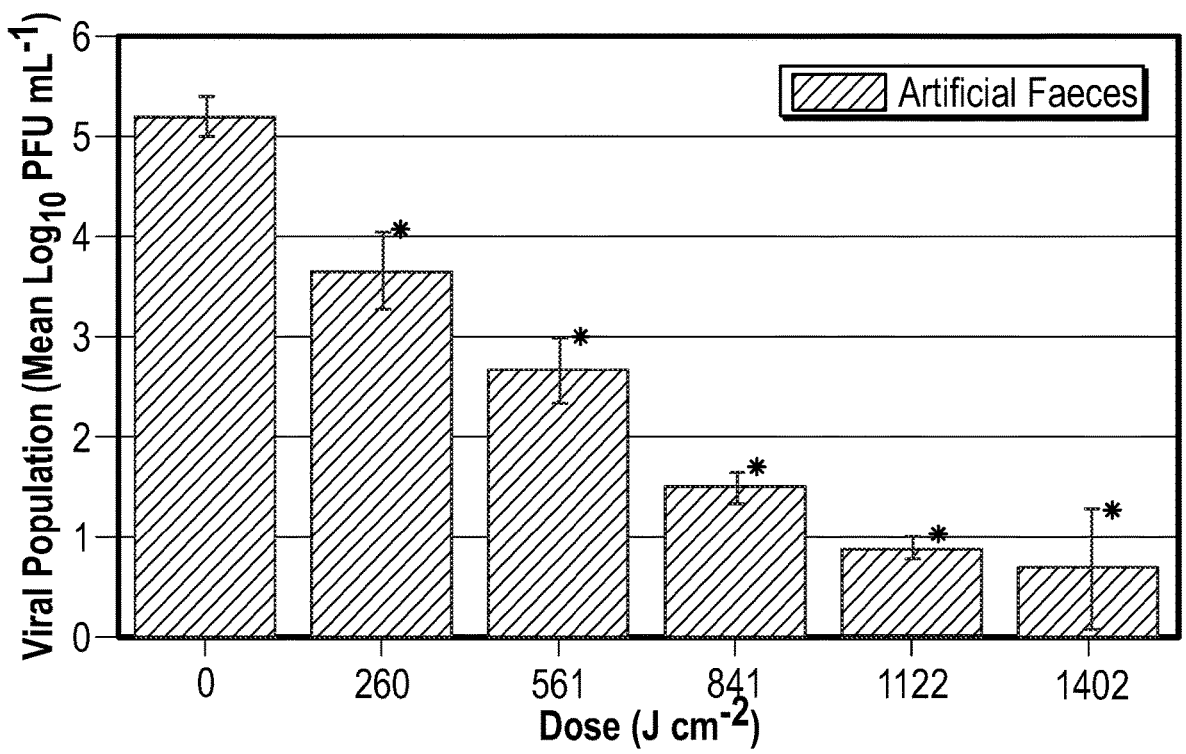
FIG. 17 shows decreasing FCV viral population in artificial faeces with increasing light doses.
Figure 18:
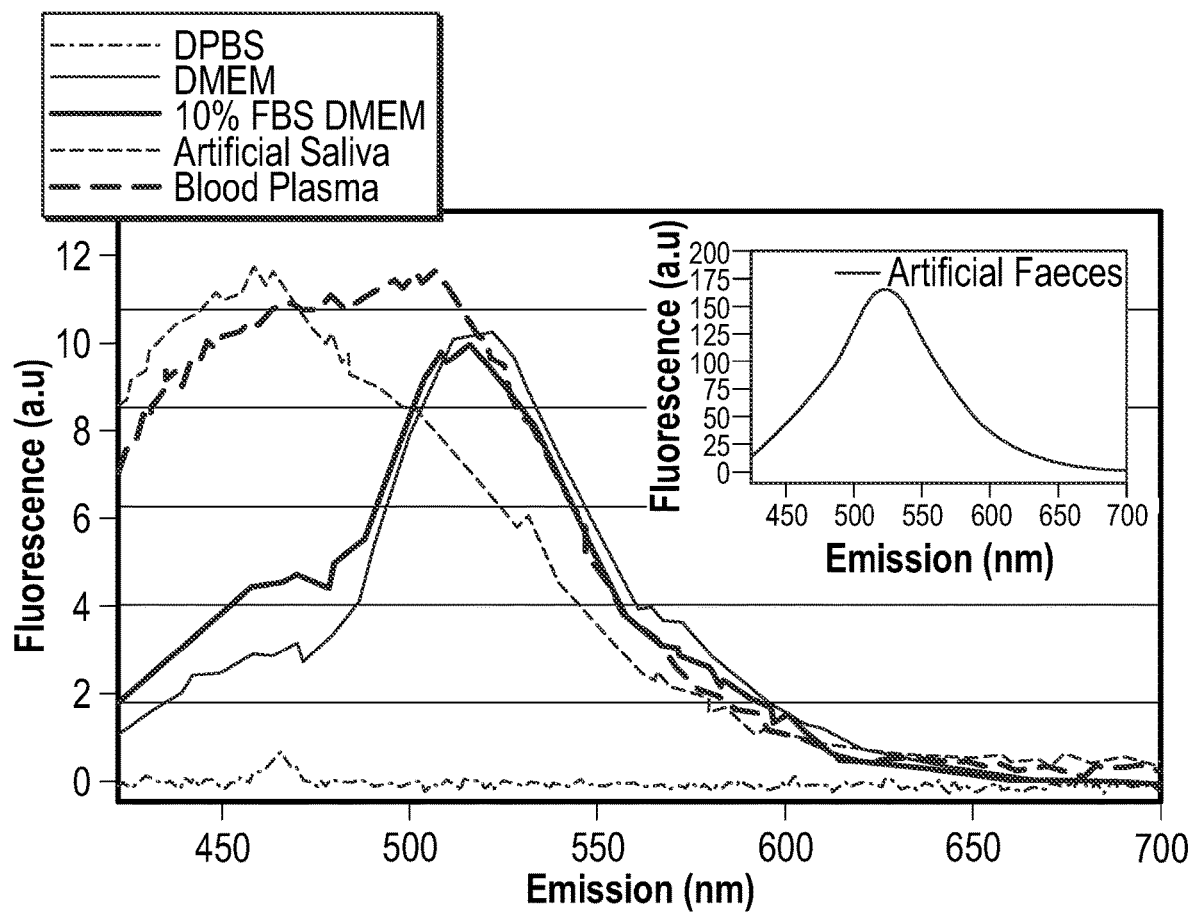
FIG. 18 illustrates an optical analysis of the suspending media, demonstrating transmission of 405 nm light in various ORM, including blood plasma, showing fluorescence emission spectra of the various ORM when excited at 405 nm.

Artificial saliva, artificial faeces, and blood plasma were selected as ORM which are biologically-relevant in terms of media in which viral particles may be found in the environment, with Norovirus regularly identified in faeces. Exposure of FCV when suspended in artificial saliva yielded results similar to those in DMEM, with a 5.1 $Log_{10}$ reduction of infectivity achieved after a dose of 421 J cm$^{-2}$ (FIG. 16). (In this case, inactivation was measured to a sensitivity of ten PFU mL$^{-1}$, as the artificial saliva in the undiluted samples adversely reacted with the FEA cells causing them to dislodge from the plate). The dose required for inactivation when suspended in blood plasma was slightly greater than when in artificial saliva, with 561 J cm$^{-2}$ required for 4.8 $log_{10}$ inactivation of FCV (FIG. 16). FCV inactivation in artificial faeces required greater doses, with 4.5 $log_{10}$ inactivation achieved after 1.4 kJ cm$^{-2}$ (FIG. 17). Control samples in artificial saliva, plasma and artificial faeces showed no significant change (P=0.618, 0.101, 0.747, respectively).

The fluorescence emission spectra (FIG. 18) of MM (DPBS) and ORM (DMEM, 10% FBS-DMEM, artificial saliva, plasma and artificial faeces) when excited at 405 nm, shows emission peaks for DMEM, 10% FBS-DMEM, plasma and artificial faeces observed between 510-520 nm and for artificial saliva at 460 nm.

TABLE 2

Comparison of the inactivation of feline calicivirus (FCV) when suspended in minimal media supplemented with riboflavin alone or alongside tyrosine, tryptophan, pyridoxine and folic acid, upon exposure to 405 nm light at an irradiance of 155 mW cm$^{-2}$.
Data points represent the mean count (n = 3) ± SD.
Asterisks indicate light-exposed samples that were significantly different to the non-exposed final control samples (P ≤ 0.05).

| Photosensitive Components | Starting Population (±St Dev) | Exposed Viral Population (±St Dev) | Non-Exposed Control Population (±St Dev) | $Log_{10}$ Reduction |
|---|---|---|---|---|
| Riboflavin | 5.01 ± 0.02 | 3.77 ± 0.61 | 5.05 ± 0.06 | 1.28* |
| Riboflavin, Tyrosine, Tryptophan, Pyridoxine Folic Acid | 5.15 ± 0.03 | 0.00 ± 0.00 | 5.12 ± 0.07 | 5.12* |

Although there has been a recent move towards using murine norovirus and tulane virus as NoV surrogates (Cromeans et al. 2014; Kniel 2014), FCV was chosen as it has physiochemical and genomic similarities to NoV, and is a well-established surrogate with a standardized cell-culture protocol (Doultree et al. 1999; Bidawid et al. 2003; Duizer et al. 2004a, b; Chander et al. 2012). Similarly, studies investigating the virucidal effects of UV-light, ozone, hydrogen peroxide vapour and cold atmospheric gas plasma technologies have also used FCV as a NoV surrogate (Nuswalen et al. 2002; Hudson et al. 2007; Bentley et al. 2012; Aboubaktar et al. 2015; Holmdahl et al. 2016).

The virucidal efficacy of 405 nm light was determined using FCV suspended in both minimal medium (MM) and organically-rich media (ORM). Exposure in MM would provide a better indication of the interaction of 405 nm light and the virus alone, whilst suspension in ORM, which is likely to contain photosensitive components, would assess how viral susceptibility can potentially be influenced by the surrounding media.

Figure 14:
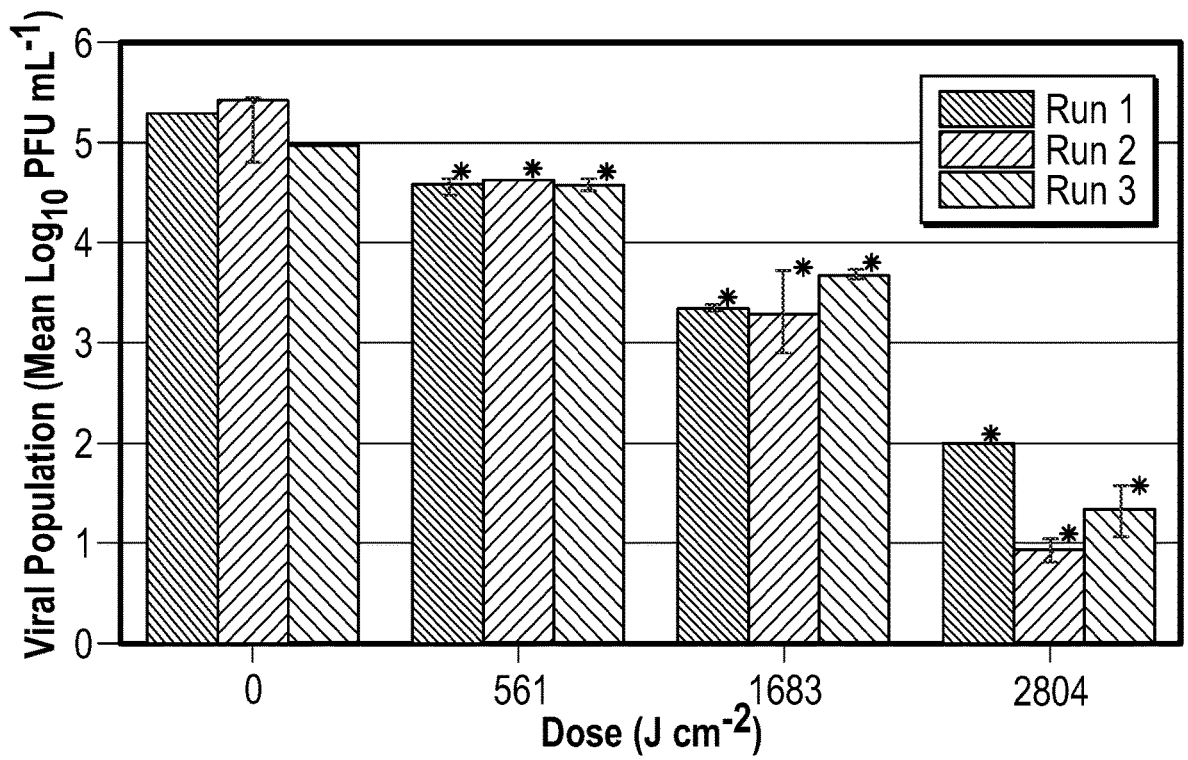
FIG. 14 shows decreasing Feline Calici Virus (FCV) viral population in a minimal medium (MM) with increasing light doses.
Figure 15:
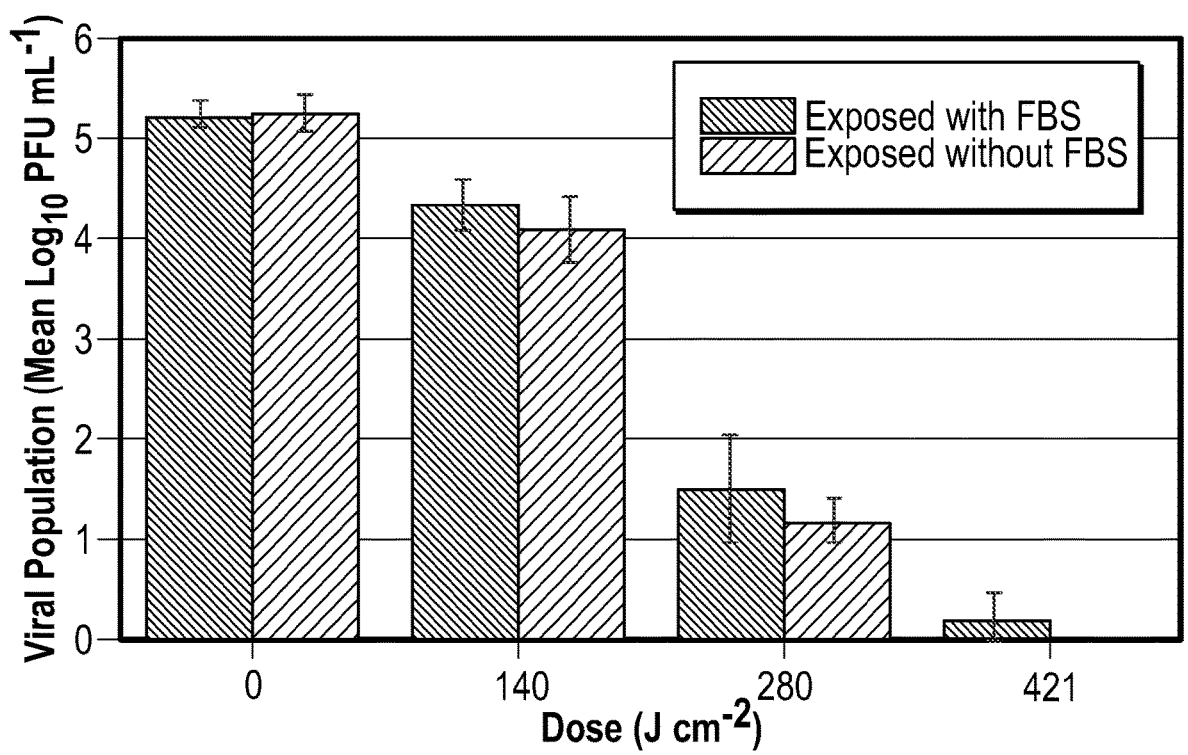
FIG. 15 shows decreasing FCV viral population in an organically-rich medium (ORM) with increasing light doses, with and without fetal bovine serum (FBS).

Successful FCV inactivation was achieved when suspended in MM, although the dose required was great, with 2.8 kJ cm$^{-2}$ achieving a 3.9 $Log_{10}$ reduction (FIG. 14). In the case of bacteria and fungi in MM, doses in the range of 18-576 J cm$^{-2}$ are typically required for 5 $Log_{10}$ inactivations (Maclean et al. 2009; Murdoch et al. 2012; Murdoch et al. 2013). The increased susceptibility of bacteria and fungi compared to viruses is accredited to the presence of endogenous photosensitive porphyrins within these cells (Hamblin et al. 2004; Maclean et al. 2008; Murdoch et al. 2013). Low sensitivity of FCV in MM occurred due to the absence of porphyrins in the viral structure, coupled with the fact that MM does not contain any photosensitive substances which absorb light at 405 nm (FIG. 18), suggesting that viral inactivation, in this case, is due to a differing mechanism.

Inactivation in MM may be associated with the LED emission spectrum extending slightly into the UVA region (FIG. 13), meaning the virus is exposed to very low-level UVA photons (~390 nm). Over an extended period, this could cause oxidative damage to proteins (Girard et al. 2011) for example to the viral capsid, and therefore contribute to the observed inactivation. Another possibility is that the small amount of 420-430 nm light emitted from the source may contribute to viral inactivation. Antiviral effects of 420-430 nm have been demonstrated against murine leukemia virus, with long exposures thought to cause photodamage to the virion-associated reverse transcription complex (Richardson & Porter 2005). Although the virus differs in structure to FCV, these findings suggest that prolonged exposure to wavelengths at the tail ends of the 405 nm LED emission spectrum such as 390 and 420 nm, as well as 405 nm, may affect the viruses' ability to infect and replicate in host cells, and have a role in the inactivation of FCV by the LEDs used in this study.

To investigate whether exposure in ORM had any effect on viral susceptibility, FCV was first suspended in DMEM with and without 10% FBS (thought to aid protection against ROS (Grzelak et al. 2001)). Results (FIG. 15) demonstrated near complete reduction in infectivity of a 10$^5$ PFU mL$^{-1}$ population after a dose of 421 J cm$^{-2}$. As can be seen in FIG. 3 slightly greater inactivation occurred when FCV was suspended in DMEM without the FBS serum additive, however, no significant difference was seen between the inactivation kinetics. As the inactivation dose of 421 J cm$^{-2}$ is 85% less than that required for a similar level of inactivation in MM, it is likely that components of the ORM are influencing FCV inactivation. A study investigating the susceptibility of bacteriophage φC31 demonstrated similar results to those of the current study: little inactivation was observed when exposed in a simple salt solution, however susceptibility was significantly enhanced when suspended in a nutrient-rich medium, with a 5.4 $Log_{10}$ reduction of φC31 achieved after exposure to 510 J cm$^{-2}$. This was hypothesized to be due to the complex protein and amino acid rich composition of the nutrient-rich medium, suggesting some components could be photosensitive and when exposed to 405 nm light in the presence of oxygen would produce ROS, damaging the bacteriophage. This same phenomenon is likely to account for the enhanced inactivation of FCV when in DMEM and 10% FBS-DMEM, as these contain a complex mixture of amino acids, vitamins and sugar, which have the potential to absorb 405 nm light (FIG. 18) and act as photosensitizers.

The photosensitization of components of DMEM has also been demonstrated upon exposure to light, with riboflavin shown to produce ROS which is further enhanced by tryptophan, tyrosine, pyridoxine and folic acid (Grzelak et al. 2001). Furthermore, blue light wavelengths are thought to be the most efficient for the photo-decomposition of riboflavin and generation of ROS (Cheng et al. 2015). To investigate this, riboflavin was added to MM with and without tyrosine, tryptophan, pyridoxine and folic acid in the same concentrations found in DMEM (Table 2 above). Results support this with only 1.3 $Log_{10}$ reduction when only riboflavin was present, however when all components were present enhanced inactivation of FCV was achieved with complete inactivation of a $10^5$ PFU $mL^{-1}$ population.

It is important to consider how light-induced inactivation would be influenced when viral particles were suspended in more biologically-relevant, naturally occurring matrices such as body fluids or secretions. As artificial saliva and artificial faeces can be prepared, these were used alongside human plasma, as model human secretions in which many viruses can be transmitted (Aitken & Jeffries, 2001).

Results (FIGS. 16 and 17) demonstrated that, similarly to inactivation in ORM (DMEM and 10% FBS-DMEM), viral susceptibility was significantly increased when suspended in these biologically-relevant fluids. Of the three model fluids used, sensitivity was highest when suspended in saliva, with a 5.1 $Log_{10}$ reduction of FCV infectivity achieved after a dose of 421 J $cm^{-2}$—the same as that observed when in ORM. Susceptibility was slightly reduced when suspended in blood plasma (4.8 $Log_{10}$ inactivation with 561 J $cm^{-2}$), and further reduced when in artificial faeces, with more than three times the dose required to achieve a 4.5 $Log_{10}$ reduction. The reduced levels of 405 nm light transmission through the plasma and artificial faeces will contribute to these slower inactivation rates. Overall, the susceptibility of FCV to 405 nm light when suspended in artificial faeces, artificial saliva, blood plasma and other organically-rich media was significantly increased when compared to susceptibility in minimal media, with 50-85% less dose required for similar levels of viral inactivation. Inactivation when suspended in these ORM is likely due to the proteins contained within the media, for example, the mucin in the artificial saliva, proteins within the plasma, and inactivated yeast within the artificial faeces, which may all be predisposed to photosensitization (demonstrated by the fluorescence peaks around 460 nm and 510-520 nm in FIG. 18). These results indicate that NoV susceptibility to 405 nm light can be enhanced when in ORM, or host secretions in which they are released such as faeces, blood and vomit. Although the consistency and transparency/opacity may differ to those used in this study, these fluids are likely to be rich in molecules which could be sensitive to 405 nm light, thereby aiding in NoV inactivation.

The disclosed technology can also provide for beneficial application of 405 nm light for the decontamination of air, surfaces and equipment in healthcare settings, as well as in other indoor locations, where transmission of viral pathogens is a significant occurrence.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Integers, characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically, magnetically, electrically, wirelessly, or otherwise coupled or linked together and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim at least all that comes within the scope of these claims.

The invention claimed is:

1. A method for inactivating pathogens in ex vivo stored blood products, comprising:
    providing a blood product storage bag having an at least partially light-transparent flexible wall;
    filling the storage bag with a blood product from at least one donor, wherein the blood product comprises blood plasma or platelet concentrates, wherein the blood product in the storage bag is free of an added photosensitizing agent, and wherein the blood product fills the storage bag to at least 50% of a full capacity of the storage bag;

sealing the storage bag after filling the storage bag with the blood product;

after sealing the storage bag, placing the filled and sealed storage bag inside a treatment chamber comprising a light source;

after placing the filled and sealed storage bag inside a treatment chamber, causing the light source to emit light having a wavelength range centered around 405 nm, with at least 90% of the light having a wavelength within 10 nm of 405 nm, wherein the emitted light penetrates through the wall of the storage bag and into the blood product, wherein the light reaching the blood product inside the storage bag has an irradiance in a range from 3 mW/cm$^2$ to 80 mW/cm$^2$, and wherein the light reaching the blood product inside storage bag inactivates pathogens in the blood product without detrimentally effecting the blood product; and after inactivating pathogens in the blood product in the sealed storage bag in the treatment chamber, coupling the sealed storage bag to a patient, unsealing the storage bag, and then transfusing the blood product from the unsealed storage bag into the patient.

2. The method of claim 1, wherein the blood product storage bag is a conventional blood product transfusion bag.

3. The method of claim 1, wherein the full capacity of the storage bag is 150 ml or 450 ml.

4. The method of claim 1, wherein the blood product fills the storage bag to at least 90% of the full capacity of the storage bag.

5. The method of claim 1, wherein the storage bag is the only container the blood product is stored in from when the blood product is received from the at least one donor to when the blood product is transfused into the patient.

6. The method of claim 5, wherein the at least one donor and the patient are different.

7. The method of claim 1, wherein the blood product stays within the storage bag with the storage bag sealed from a time when the storage bag is placed in the treatment chamber until a time when the storage bag is coupled to the patient.

8. The method of claim 7, wherein more than 24 hours elapses between the time when the storage bag is placed in the treatment chamber until the time when the storage bag is coupled to the patient.

9. The method of claim 1, wherein the light reaching the blood product inside the storage bag has an irradiance in a range from 3 mW/cm$^2$ to 10 mW/cm$^2$.

10. The method of claim 1, wherein the method further comprises varying intensity of the light emitted by the light source during treatment of the blood product in the storage bag in the treatment chamber.

11. The method of claim 10, wherein varying the intensity of the light emitted by the light source during treatment comprises:

causing the intensity of the emitted light to be at a first level during a pathogen inactivation period; and causing the intensity of the emitted light to be at a second level during a maintenance period subsequent to the pathogen inactivation period while the storage bag is still inside the treatment chamber, the second level being lower than the first level.

12. The method of claim 1, wherein the blood product is irradiated within the treatment chamber for at least one hour.

13. The method of claim 1, wherein the blood product is irradiated within the treatment chamber for at least four hours.

14. The method of claim 1, further comprising agitating the storage bag while the emitted light penetrates through the wall of the storage bag and into the blood product such that the blood product moves within the storage bag.

15. The method of claim 14, wherein agitating comprises causing the storage bag to reciprocate at from 30 to 100 reciprocations per minute.

16. The method of claim 1, further comprising circulating air around the storage bag within the treatment chamber while the emitted light penetrates through the wall of the storage bag to maintain a desired temperature range for the storage bag and the blood product.

17. The method of claim 1, wherein the light reaching the blood product inside storage bag is sufficient to inactivate bacteria, viruses, and fungi in the blood product.

18. The method of claim 1, wherein the storage bag comprises polyvinyl chloride.

19. The method of claim 18, wherein the storage bag is free of Di(2-ethylhexyl) phthalate (DEHP).

* * * * *